US011525104B2

(12) United States Patent
Tan et al.

(10) Patent No.: US 11,525,104 B2
(45) Date of Patent: Dec. 13, 2022

(54) POROUS DISSOLVABLE SOLID STRUCTURE

(71) Applicant: The Procter & Gamble Company, Cincinnati, OH (US)

(72) Inventors: Hongsing Tan, Beijing (CN); Robert Wayne Glenn, Jr., Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 113 days.

(21) Appl. No.: 16/953,975

(22) Filed: Nov. 20, 2020

(65) Prior Publication Data

US 2021/0147763 A1 May 20, 2021

(30) Foreign Application Priority Data

Nov. 20, 2019 (WO) ................ PCT/CN2019/119586

(51) Int. Cl.
| | | |
|---|---|---|
| C11D 17/00 | (2006.01) | |
| C11D 1/12 | (2006.01) | |
| C11D 1/90 | (2006.01) | |
| C11D 1/94 | (2006.01) | |
| C11D 3/20 | (2006.01) | |
| C11D 3/37 | (2006.01) | |
| C11D 1/88 | (2006.01) | |
| C11D 1/10 | (2006.01) | |
| C11D 1/28 | (2006.01) | |

(52) U.S. Cl.
CPC .............. *C11D 1/94* (2013.01); *C11D 3/2065* (2013.01); *C11D 3/3753* (2013.01); *C11D 17/0065* (2013.01); *C11D 1/10* (2013.01); *C11D 1/123* (2013.01); *C11D 1/28* (2013.01); *C11D 1/88* (2013.01); *C11D 1/90* (2013.01)

(58) Field of Classification Search
None
See application file for complete search history.

(56) References Cited

U.S. PATENT DOCUMENTS

| | | |
|---|---|---|
| 1,421,350 A | 6/1922 | Powell |
| 2,356,168 A | 8/1944 | Mabley |
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,613,185 A | 10/1952 | Marshall |
| 2,658,072 A | 11/1953 | Milton |
| 2,694,668 A | 11/1954 | Fricke |
| 2,809,971 A | 10/1957 | Jack |
| 3,152,046 A | 10/1964 | Maria |
| 3,236,733 A | 2/1966 | Karsten et al. |
| 3,321,425 A | 5/1967 | Karl-ludwig et al. |
| 3,332,880 A | 7/1967 | Adriaan et al. |
| 3,426,440 A | 2/1969 | Shen et al. |
| 3,428,478 A | 2/1969 | Donaldson et al. |
| 3,463,308 A | 8/1969 | Deneke |
| 3,489,688 A | 1/1970 | Pospischil |
| 3,570,122 A | 3/1971 | Willimas |
| 3,589,007 A | 6/1971 | Walton |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |
| 3,929,678 A | 12/1975 | Laughlin |
| 3,967,921 A | 7/1976 | Haberli et al. |
| 4,020,156 A | 4/1977 | Murray et al. |
| 4,024,078 A | 5/1977 | Gilbert et al. |
| 4,051,081 A | 9/1977 | Jabs et al. |
| 4,089,945 A | 5/1978 | Brinkman et al. |
| 4,149,551 A | 4/1979 | Benjamin et al. |
| 4,185,125 A | 1/1980 | Kimura et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,323,683 A | 4/1982 | Bolich, Jr. et al. |
| 4,345,080 A | 8/1982 | Bolich, Jr. |
| D266,829 S | 11/1982 | Yoshizawa et al. |
| 4,379,753 A | 4/1983 | Bolich, Jr. |
| 4,381,919 A | 5/1983 | Jacquet et al. |
| 4,422,853 A | 12/1983 | Jacquet et al. |
| 4,470,982 A | 9/1984 | Winkler |
| 4,507,280 A | 3/1985 | Pohl et al. |
| 4,529,586 A | 7/1985 | De et al. |
| 4,536,361 A | 8/1985 | Torobin |

(Continued)

FOREIGN PATENT DOCUMENTS

| | | |
|---|---|---|
| CA | 166297 | 5/2018 |
| CA | 169627 S | 5/2018 |

(Continued)

OTHER PUBLICATIONS

All Office Actions; U.S. Appl. No. 17/357,119, filed Jun. 24, 2021.
All Office Actions; U.S. Appl. No. 29/815,500, filed Nov. 15, 2021.
Raymond C Rowe et al., Polyvinyl Alcohol, Handbook of Pharmaceutical Excipients, 2009, Sixth Edition, Pharmaceutical Press, 564-565.
Sahin et al. "A Study on Physical and Chemical Properties of Cellulose Paper Immersed in Various Solvent Mixtures" International Journal Of Molecular Sciences, Jan. 2008; 9(1): 78-88.
All Office Actions; U.S. Appl. No. 29/819,499, filed Dec. 15, 2021.
Color Keeper [online], [site visited Oct. 18, 2021]. Available from internet, URL: https://shopgemz.com/products/color-keeper?variant=13094595002434&utm_source=google&utm_medium=cpc&utm_campaign=Shopping&gclid=Cj0KCQjw5JSLBhCxARIsAHgO2Sd AT7LTehpyxM1qTGtnFETDa1Nuo9_cQSOpPwCmsmmdGA1Y0USekQEaAh0iEALw_wcB (Year: 2021).

(Continued)

*Primary Examiner* — Lorna M Douyon
(74) *Attorney, Agent, or Firm* — Alexandra S. Anoff

(57) ABSTRACT

A porous dissolvable solid can include an isethionate surfactant; a non-sulfate anionic surfactant; and an amphoteric surfactant, a zwitterionic surfactant, or a combination thereof.

16 Claims, No Drawings

(56) References Cited

U.S. PATENT DOCUMENTS

| | | |
|---|---|---|
| 4,565,647 A | 1/1986 | Llenado |
| D286,450 S | 10/1986 | Tovey |
| 4,635,351 A | 1/1987 | Koch et al. |
| 4,663,158 A | 5/1987 | Wolfram et al. |
| 4,710,374 A | 12/1987 | Grollier et al. |
| 4,727,410 A | 2/1988 | Higgins, III |
| 4,822,613 A | 4/1989 | Rodero |
| 4,885,107 A | 12/1989 | Wetzel |
| 4,976,953 A | 12/1990 | Orr et al. |
| 4,990,280 A | 2/1991 | Thorengaard |
| 5,055,384 A | 10/1991 | Kuehnert |
| 5,061,481 A | 10/1991 | Suzuki et al. |
| 5,062,889 A | 11/1991 | Hoehl et al. |
| 5,062,994 A | 11/1991 | Imperatori |
| 5,094,853 A | 3/1992 | Hagarty |
| 5,098,636 A | 3/1992 | Balk |
| 5,100,657 A | 3/1992 | Ansher-jackson et al. |
| 5,100,658 A | 3/1992 | Bolich, Jr. et al. |
| 5,102,129 A | 4/1992 | Roberts |
| 5,104,646 A | 4/1992 | Bolich, Jr. |
| 5,106,609 A | 4/1992 | Bolich, Jr. |
| 5,166,276 A | 11/1992 | Hayama et al. |
| D334,420 S | 3/1993 | Copeland et al. |
| 5,220,033 A | 6/1993 | Kamei et al. |
| 5,261,426 A | 11/1993 | Kellett et al. |
| 5,280,079 A | 1/1994 | Allen et al. |
| RE34,584 E | 4/1994 | Grote et al. |
| D351,345 S | 10/1994 | Geho |
| 5,391,368 A | 2/1995 | Gerstein |
| D357,115 S | 4/1995 | Ashley et al. |
| 5,409,703 A | 4/1995 | Mcanalley et al. |
| D358,025 S | 5/1995 | Martin et al. |
| 5,415,810 A | 5/1995 | Lee |
| 5,429,628 A | 7/1995 | Trinh et al. |
| 5,455,114 A | 10/1995 | Ohmory |
| 5,457,895 A | 10/1995 | Thompson et al. |
| 5,458,433 A | 10/1995 | Stastny |
| 5,476,597 A | 12/1995 | Sakata et al. |
| 5,501,238 A | 3/1996 | Borstel et al. |
| 5,533,638 A | 7/1996 | Reiker |
| 5,580,481 A | 12/1996 | Sakata et al. |
| 5,582,786 A | 12/1996 | Brunskill et al. |
| D378,180 S | 2/1997 | Hayes |
| 5,660,845 A | 8/1997 | Trinh et al. |
| 5,672,576 A | 9/1997 | Behrens et al. |
| 5,673,576 A | 10/1997 | Chen et al. |
| 5,674,478 A | 10/1997 | Dodd |
| 5,750,122 A | 5/1998 | Evans |
| 5,780,047 A | 7/1998 | Kamiya et al. |
| D398,847 S | 9/1998 | Wyslotsky |
| D399,260 S | 10/1998 | Thimote |
| 5,849,378 A | 12/1998 | Gask |
| D407,640 S | 4/1999 | Crapser et al. |
| D408,223 S | 4/1999 | Henry |
| 5,911,224 A | 6/1999 | Berger |
| 5,925,603 A | 7/1999 | D'Angelo |
| 5,955,419 A | 9/1999 | Barket, Jr. et al. |
| D416,103 S | 11/1999 | Hashmi |
| 5,976,454 A | 11/1999 | Sterzel et al. |
| D418,415 S | 1/2000 | Hayes |
| D418,750 S | 1/2000 | Blin |
| 6,010,719 A | 1/2000 | Remon et al. |
| 6,029,808 A | 2/2000 | Peck et al. |
| 6,034,043 A | 3/2000 | Fujiwara |
| D427,902 S | 7/2000 | Hayes |
| 6,106,849 A | 8/2000 | Malkan et al. |
| 6,177,391 B1 | 1/2001 | Zafar |
| 6,200,949 B1 | 3/2001 | Reijmer et al. |
| D441,869 S | 5/2001 | Bloor et al. |
| D442,353 S | 5/2001 | Macias |
| D442,739 S | 5/2001 | Friesenhahn |
| D443,389 S | 6/2001 | Friesenhahn |
| D448,802 S | 10/2001 | Lariviere, Jr. et al. |
| D449,881 S | 10/2001 | Mock, Sr. |
| D450,378 S | 11/2001 | Minakuchi et al. |
| 6,365,142 B1 | 4/2002 | Tamura |
| D462,900 S | 9/2002 | Yamada et al. |
| 6,458,754 B1 | 10/2002 | Velazquez et al. |
| D465,303 S | 11/2002 | Friesenhahn |
| 6,503,521 B1 | 1/2003 | Atis et al. |
| 6,525,034 B2 | 2/2003 | Dalrymple et al. |
| D479,561 S | 9/2003 | Meyer |
| D484,749 S | 1/2004 | Garraway |
| D489,162 S | 5/2004 | Dings-plooij |
| 6,790,814 B1 | 9/2004 | Marin |
| 6,800,295 B2 | 10/2004 | Fox |
| 6,808,375 B2 | 10/2004 | Kloetzer |
| 6,825,161 B2 | 11/2004 | Shefer et al. |
| 6,831,046 B2 | 12/2004 | Carew et al. |
| 6,846,784 B2 | 1/2005 | Engel et al. |
| 6,878,368 B2 | 4/2005 | Ohta et al. |
| D509,935 S | 9/2005 | Burt |
| 6,943,200 B1 | 9/2005 | Corrand et al. |
| D515,915 S | 2/2006 | Karim |
| 7,015,181 B2 | 3/2006 | Lambino |
| 7,208,460 B2 | 4/2007 | Shefer et al. |
| D549,051 S | 8/2007 | Nordwall |
| 7,285,520 B2 | 10/2007 | Krzysik |
| 7,387,787 B2 | 6/2008 | Fox |
| D576,753 S | 9/2008 | Mukai |
| D577,332 S | 9/2008 | Moore |
| D578,881 S | 10/2008 | Friedland |
| D588,332 S | 3/2009 | Phelan |
| 7,832,552 B2 | 11/2010 | Newman |
| 7,846,462 B2 | 12/2010 | Spadini et al. |
| 7,892,992 B2 | 2/2011 | Kamada et al. |
| 7,901,696 B2 | 3/2011 | Eknoian et al. |
| D640,921 S | 7/2011 | Caldwell |
| D644,541 S | 9/2011 | Schrader et al. |
| D651,096 S | 12/2011 | Nakagiri |
| D655,154 S | 3/2012 | Amos |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,357,728 B2 | 1/2013 | Butler et al. |
| 8,367,596 B2 | 2/2013 | Fossum et al. |
| D680,882 S | 4/2013 | Logue |
| 8,415,287 B2 | 4/2013 | Glenn, Jr. et al. |
| D682,622 S | 5/2013 | Keys |
| 8,461,090 B2 | 6/2013 | Glenn, Jr. et al. |
| 8,461,091 B2 | 6/2013 | Glenn, Jr. |
| 8,466,099 B2 | 6/2013 | Glenn, Jr. et al. |
| D685,436 S | 7/2013 | Menting |
| 8,476,211 B2 | 7/2013 | Glenn, Jr. et al. |
| 8,541,081 B1 | 9/2013 | Ranganathan et al. |
| 8,546,640 B2 | 10/2013 | Popovsky et al. |
| D694,621 S | 12/2013 | Mccarthy |
| 8,723,333 B2 | 5/2014 | Park et al. |
| 8,765,170 B2 | 7/2014 | Glenn, Jr. |
| D712,159 S | 9/2014 | Clerici et al. |
| D712,822 S | 9/2014 | Brusaw et al. |
| 9,062,186 B2 | 6/2015 | Longdon et al. |
| D739,227 S | 9/2015 | Mitchell et al. |
| D740,928 S | 10/2015 | Bruining et al. |
| 9,198,838 B2 | 12/2015 | Glenn, Jr. |
| D748,240 S | 1/2016 | Goode |
| D769,522 S | 10/2016 | Venet |
| D771,788 S | 11/2016 | Duckwitz |
| D774,086 S | 12/2016 | Montes et al. |
| D775,198 S | 12/2016 | Montes et al. |
| 9,539,444 B2 | 1/2017 | Kinoshita et al. |
| D778,026 S | 2/2017 | Roetheli |
| D793,025 S | 8/2017 | Slusarczyk et al. |
| D797,551 S | 9/2017 | Chatterton |
| D798,143 S | 9/2017 | Chatterton |
| D808,583 S | 1/2018 | Zietek |
| D811,922 S | 3/2018 | Lefave |
| D811,935 S | 3/2018 | Hughes |
| D819,836 S | 6/2018 | Noël |

(56) References Cited

U.S. PATENT DOCUMENTS

| | | |
|---|---|---|
| D848,102 S | 5/2019 | Carlson et al. |
| D850,041 S | 5/2019 | Endle |
| 10,294,586 B2 | 5/2019 | Sivik et al. |
| D851,344 S | 6/2019 | Carlson et al. |
| D857,156 S | 8/2019 | Hani |
| D857,242 S | 8/2019 | Darrow et al. |
| D857,929 S | 8/2019 | Darrow et al. |
| D862,020 S | 10/2019 | Gorrell et al. |
| D863,600 S | 10/2019 | Chao |
| D864,507 S | 10/2019 | Stoughton et al. |
| D866,105 S | 11/2019 | Carlson et al. |
| D866,891 S | 11/2019 | Carlson et al. |
| D866,892 S | 11/2019 | Hunt et al. |
| D866,893 S | 11/2019 | Hunt et al. |
| D867,717 S | 11/2019 | Chavez |
| D868,159 S | 11/2019 | Swisher et al. |
| D868,953 S | 12/2019 | Mckendree |
| 10,569,286 B2 | 2/2020 | Anderson et al. |
| D878,694 S | 3/2020 | Carlson et al. |
| 10,694,917 B2 | 6/2020 | Dreher et al. |
| D901,115 S | 11/2020 | Carlson et al. |
| D903,152 S | 11/2020 | Chao |
| D906,802 S | 1/2021 | Chi |
| D910,434 S | 2/2021 | Tan et al. |
| D910,457 S | 2/2021 | Lee |
| D921,166 S | 6/2021 | Meyers |
| D933,095 S | 10/2021 | Heiner et al. |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada et al. |
| 2002/0187181 A1 | 12/2002 | Godbey et al. |
| 2003/0018242 A1 | 1/2003 | Hursh et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |
| 2003/0080150 A1 | 5/2003 | Cowan |
| 2003/0099691 A1 | 5/2003 | Lydzinski et al. |
| 2003/0099692 A1 | 5/2003 | Lydzinski et al. |
| 2003/0141662 A1 | 7/2003 | Kost et al. |
| 2003/0166489 A1 | 9/2003 | Van et al. |
| 2003/0180242 A1 | 9/2003 | Eccard et al. |
| 2003/0186826 A1 | 10/2003 | Eccard et al. |
| 2003/0194416 A1 | 10/2003 | Shefer |
| 2003/0199412 A1 | 10/2003 | Gupta |
| 2003/0207776 A1 | 11/2003 | Shefer et al. |
| 2003/0209166 A1 | 11/2003 | Vanmaele et al. |
| 2003/0215522 A1 | 11/2003 | Johnson et al. |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0048771 A1 | 3/2004 | Mcdermott |
| 2004/0053808 A1 | 3/2004 | Raehse et al. |
| 2004/0059055 A1 | 3/2004 | Inada |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey et al. |
| 2004/0118852 A1 | 6/2004 | Barmore et al. |
| 2004/0126585 A1 | 7/2004 | Kerins et al. |
| 2004/0175404 A1 | 9/2004 | Shefer |
| 2004/0180597 A1 | 9/2004 | Kamada |
| 2004/0202632 A1 | 10/2004 | Gott et al. |
| 2004/0206270 A1 | 10/2004 | Vanmaele et al. |
| 2004/0242097 A1 | 12/2004 | Hasenoehrl |
| 2004/0242772 A1 | 12/2004 | Huth et al. |
| 2005/0069575 A1 | 3/2005 | Fox |
| 2005/0118237 A1 | 6/2005 | Krzysik et al. |
| 2005/0136780 A1 | 6/2005 | Clark et al. |
| 2005/0137272 A1 | 6/2005 | Gaserod |
| 2005/0159730 A1 | 7/2005 | Kathrani et al. |
| 2005/0202992 A1 | 9/2005 | Grandio et al. |
| 2005/0220745 A1 | 10/2005 | Lu |
| 2005/0232954 A1 | 10/2005 | Yoshinari et al. |
| 2005/0272836 A1 | 12/2005 | Yaginuma et al. |
| 2005/0287106 A1 | 12/2005 | Legendre |
| 2006/0002880 A1 | 1/2006 | Peffly et al. |
| 2006/0013869 A1 | 1/2006 | Ignatious |
| 2006/0052263 A1 | 3/2006 | Roreger et al. |
| 2006/0064510 A1 | 3/2006 | Low et al. |
| 2006/0078528 A1 | 4/2006 | Yang et al. |
| 2006/0078529 A1 | 4/2006 | Uchida et al. |
| 2006/0128592 A1 | 6/2006 | Ross |
| 2006/0159730 A1 | 7/2006 | Simon |
| 2006/0228319 A1 | 10/2006 | Vona et al. |
| 2006/0274263 A1 | 12/2006 | Yacktman et al. |
| 2007/0028939 A1 | 2/2007 | Mareri et al. |
| 2007/0099813 A1 | 5/2007 | Luizzi |
| 2007/0110792 A9 | 5/2007 | Simon |
| 2007/0135528 A1 | 6/2007 | Butler et al. |
| 2007/0149435 A1 | 6/2007 | Koenig et al. |
| 2007/0225388 A1 | 9/2007 | Cooper et al. |
| 2008/0019935 A1 | 1/2008 | Khan |
| 2008/0035174 A1 | 2/2008 | Aubrun-sonneville |
| 2008/0083420 A1 | 4/2008 | Glenn et al. |
| 2008/0090939 A1 | 4/2008 | Netravali et al. |
| 2008/0131695 A1 | 6/2008 | Aouad et al. |
| 2008/0138492 A1 | 6/2008 | Cingotti |
| 2008/0152894 A1 | 6/2008 | Beihoffer et al. |
| 2008/0153730 A1 | 6/2008 | Tsaur |
| 2008/0215023 A1 | 9/2008 | Scavone et al. |
| 2008/0276178 A1 | 11/2008 | Fadell et al. |
| 2008/0292669 A1 | 11/2008 | Deng et al. |
| 2008/0293839 A1 | 11/2008 | Stobby |
| 2009/0197787 A1 | 8/2009 | Venet et al. |
| 2009/0232873 A1 | 9/2009 | Glenn, Jr. et al. |
| 2009/0263342 A1 | 10/2009 | Glenn, Jr. |
| 2010/0018641 A1 | 1/2010 | Branham |
| 2010/0150976 A1 | 6/2010 | Schnitzler |
| 2010/0167971 A1 | 7/2010 | Glenn, Jr. et al. |
| 2010/0173817 A1 | 7/2010 | Glenn, Jr. et al. |
| 2010/0179083 A1 | 7/2010 | Glenn, Jr. et al. |
| 2010/0279905 A1 | 11/2010 | Glenn, Jr. |
| 2010/0286011 A1 | 11/2010 | Glenn, Jr. et al. |
| 2010/0291165 A1 | 11/2010 | Glenn, Jr. et al. |
| 2011/0023240 A1 | 2/2011 | Fossum |
| 2011/0027328 A1 | 2/2011 | Baig et al. |
| 2011/0028373 A1 | 2/2011 | Fossum et al. |
| 2011/0028374 A1 | 2/2011 | Fossum et al. |
| 2011/0033509 A1 | 2/2011 | Simon |
| 2011/0165110 A1 | 7/2011 | Kinoshita et al. |
| 2011/0182956 A1 | 7/2011 | Glenn, Jr. et al. |
| 2011/0189246 A1 | 8/2011 | Glenn, Jr. et al. |
| 2011/0189247 A1 | 8/2011 | Glenn, Jr. |
| 2011/0195098 A1 | 8/2011 | Glenn, Jr. |
| 2011/0250256 A1 | 10/2011 | Hyun-oh et al. |
| 2011/0287687 A1 | 11/2011 | Kramer et al. |
| 2012/0021026 A1 | 1/2012 | Glenn, Jr. |
| 2012/0052036 A1 | 3/2012 | Glenn, Jr. |
| 2012/0052037 A1 | 3/2012 | Sivik et al. |
| 2012/0107534 A1 | 5/2012 | Wnuk et al. |
| 2012/0237576 A1 | 9/2012 | Gordon |
| 2012/0270029 A1 | 10/2012 | Glenn, Jr. et al. |
| 2012/0288693 A1 | 11/2012 | Stanley et al. |
| 2012/0294823 A1 | 11/2012 | Aramwit |
| 2012/0321580 A1 | 12/2012 | Glenn, Jr. |
| 2013/0236520 A1 | 9/2013 | Popovsky et al. |
| 2013/0303419 A1 | 11/2013 | Glenn, Jr. et al. |
| 2014/0105946 A1* | 4/2014 | Glenn, Jr. .............. A61Q 19/00 510/447 |
| 2014/0271744 A1 | 9/2014 | Glenn, Jr. et al. |
| 2014/0329428 A1 | 11/2014 | Glenn, Jr. |
| 2015/0102307 A1 | 4/2015 | Tajima et al. |
| 2015/0297494 A1 | 10/2015 | Mao |
| 2015/0313803 A1 | 11/2015 | Lynch et al. |
| 2015/0313804 A1 | 11/2015 | Lynch et al. |
| 2015/0313805 A1 | 11/2015 | Lynch et al. |
| 2015/0313806 A1 | 11/2015 | Lynch et al. |
| 2015/0313807 A1 | 11/2015 | Lynch et al. |
| 2015/0313808 A1 | 11/2015 | Lynch et al. |
| 2015/0313809 A1 | 11/2015 | Lynch et al. |
| 2015/0315350 A1 | 11/2015 | Mao et al. |

(56) References Cited

U.S. PATENT DOCUMENTS

| | | |
|---|---|---|
| 2016/0008235 A1 | 1/2016 | Sivik et al. |
| 2016/0101026 A1 | 4/2016 | Pratt |
| 2016/0101204 A1 | 4/2016 | Lynch |
| 2016/0143827 A1 | 5/2016 | Castan Barberan et al. |
| 2016/0250109 A1 | 9/2016 | Dreher et al. |
| 2016/0367104 A1 | 12/2016 | Dreher et al. |
| 2017/0121641 A1 | 5/2017 | Smith |
| 2017/0335080 A1 | 11/2017 | Mao et al. |
| 2018/0110710 A1* | 4/2018 | Zhao ................. C11D 1/37 |
| 2018/0140469 A1 | 5/2018 | Kane et al. |
| 2018/0311135 A1 | 11/2018 | Chang et al. |
| 2018/0333339 A1 | 11/2018 | Hamersky |
| 2018/0334644 A1 | 11/2018 | Hamersky et al. |
| 2019/0015875 A1 | 1/2019 | Gardner, Jr. et al. |
| 2019/0282457 A1 | 9/2019 | Pratt |
| 2019/0282461 A1 | 9/2019 | Glassmeyer |
| 2019/0350819 A1 | 11/2019 | Hamersky et al. |
| 2020/0093710 A1 | 3/2020 | Hamersky |
| 2020/0214946 A1 | 7/2020 | Chan et al. |
| 2020/0308360 A1 | 10/2020 | Mao et al. |
| 2020/0405587 A1 | 12/2020 | Song |
| 2021/0000733 A1 | 1/2021 | Hilvert |
| 2021/0094744 A1 | 4/2021 | Benson et al. |
| 2021/0107263 A1 | 4/2021 | Bartolucci et al. |
| 2021/0401677 A1 | 12/2021 | Song |

FOREIGN PATENT DOCUMENTS

| | | |
|---|---|---|
| CN | 1138091 | 12/1996 |
| CN | 1219388 | 6/1999 |
| CN | 1268558 | 10/2000 |
| CN | 1357613 A | 7/2002 |
| CN | 1454231 A | 11/2003 |
| CN | 1473194 A | 2/2004 |
| CN | 1530431 A | 9/2004 |
| CN | 1583991 A | 2/2005 |
| CN | 1726074 A | 1/2006 |
| CN | 3648760 | 5/2007 |
| CN | 102006852 A | 4/2011 |
| CN | 301666535 | 9/2011 |
| CN | 102647973 A | 8/2012 |
| CN | 103282015 A | 9/2013 |
| CN | 103735428 A | 4/2014 |
| CN | 104040061 A | 9/2014 |
| CN | 304115833 | 4/2017 |
| CN | 106726634 A | 5/2017 |
| CN | 106728634 A | 5/2017 |
| CN | 304537587 | 3/2018 |
| CN | 109589279 B | 3/2020 |
| DE | 19607851 A1 | 9/1997 |
| DE | 10331767 A1 | 2/2005 |
| DE | 100932 | 4/2018 |
| DE | 100938 | 4/2018 |
| DE | 101063 | 5/2018 |
| DE | 101100 | 5/2018 |
| DE | 101101 | 5/2018 |
| EP | 0392608 A2 | 10/1990 |
| EP | 609808 A1 | 8/1994 |
| EP | 0858828 A1 | 8/1998 |
| EP | 0948960 A2 | 10/1999 |
| EP | 1214879 A2 | 6/2002 |
| EP | 1217987 B1 | 12/2004 |
| EP | 1574561 A1 | 9/2005 |
| EP | 1160311 B1 | 3/2006 |
| EP | 1958532 A2 | 8/2008 |
| EP | 2085434 A1 | 8/2009 |
| EP | 1317916 B1 | 10/2010 |
| FR | 2871685 A1 | 12/2005 |
| FR | 2886845 A1 | 12/2006 |
| GB | 2235204 A | 2/1991 |
| GB | 2355008 A | 4/2001 |
| GB | 2378407 A | 2/2003 |
| JP | 58021608 | 2/1983 |
| JP | S58216109 A | 12/1983 |
| JP | S6272609 A | 4/1987 |
| JP | S6272610 A | 4/1987 |
| JP | S6281432 A | 4/1987 |
| JP | H01172319 A | 7/1989 |
| JP | H01313418 A | 12/1989 |
| JP | H0275650 A | 3/1990 |
| JP | H05344873 A | 12/1993 |
| JP | H0617083 A | 1/1994 |
| JP | 0753349 | 2/1995 |
| JP | H0789852 A | 4/1995 |
| JP | H08325133 A | 12/1996 |
| JP | H09216909 A | 8/1997 |
| JP | H10251371 A | 9/1998 |
| JP | H11513053 A | 11/1999 |
| JP | 2000053998 A | 2/2000 |
| JP | 2000229841 A | 8/2000 |
| JP | 2001519376 A | 10/2001 |
| JP | 2001520983 A | 11/2001 |
| JP | 2002226895 A | 8/2002 |
| JP | 2003073700 A | 3/2003 |
| JP | 2003082397 A | 3/2003 |
| JP | 2004509198 A | 3/2004 |
| JP | 2004256799 A | 9/2004 |
| JP | 2004345983 A | 12/2004 |
| JP | 2005171063 A | 6/2005 |
| JP | 2005538202 A | 12/2005 |
| JP | 2006056835 A | 3/2006 |
| JP | 2007001889 A | 1/2007 |
| JP | 2007091954 A | 4/2007 |
| JP | 2007197365 A | 8/2007 |
| JP | 2007197540 A | 8/2007 |
| KR | 20020003442 A | 1/2002 |
| WO | 8301943 A1 | 6/1983 |
| WO | 9514495 A1 | 6/1995 |
| WO | 9951715 A1 | 10/1999 |
| WO | 0042992 A2 | 7/2000 |
| WO | 0107194 A1 | 2/2001 |
| WO | 0119948 A1 | 3/2001 |
| WO | 0125393 A1 | 4/2001 |
| WO | 200125322 A1 | 4/2001 |
| WO | 2001024770 A1 | 4/2001 |
| WO | 2001054667 A1 | 8/2001 |
| WO | 0238722 A2 | 5/2002 |
| WO | 2004032859 A1 | 4/2004 |
| WO | 2004041991 A1 | 5/2004 |
| WO | 2005003423 A1 | 1/2005 |
| WO | 2005070374 A1 | 8/2005 |
| WO | 2005075547 A1 | 8/2005 |
| WO | 2007033598 A1 | 3/2007 |
| WO | 2007093558 A1 | 8/2007 |
| WO | 2007102119 A1 | 9/2007 |
| WO | 2008104954 A2 | 9/2008 |
| WO | 2009019571 A1 | 2/2009 |
| WO | 2009095891 A1 | 8/2009 |
| WO | 2010077627 A2 | 7/2010 |
| WO | 2010085569 A1 | 7/2010 |
| WO | 2012120199 A1 | 9/2012 |
| WO | 2019001940 A1 | 1/2019 |

OTHER PUBLICATIONS

Paper Pieces Hexagons, announced 2018 [online], [site visited Oct. 14, 2021]. Available from internet, URL:https://www.amazon.com/Paper-Pieces-HEX100B-Hexagons-1200pc/dp/B07DVYV2HN/ (Year: 2018).

Rounded hexagon shape, announced 2016 [online], [site visited Oct. 20, 2021], Available from internet, URL:https://www.vexels.com/png-svg/preview/139199/rounded-hexagon-shape (Year: 2016).

Adhesives Research (Pennsylvania, http://12.4.33.51/news/apresmed.htm).

All final and non-final office actions for U.S. Appl. No. 14/690,593.
All final and non-final office actions for U.S. Appl. No. 15/665,886.
All final and non-final office actions for U.S. Appl. No. 16/431,028.
All final and non-final office actions for U.S. Appl. No. 16/431,115.
All final and non-final office actions for U.S. Appl. No. 16/577,120.
All final and non-final office actions for U.S. Appl. No. 16/589,504.
All final and non-final office actions for U.S. Appl. No. 16/901,548.
All final and non-final office actions for U.S. Appl. No. 16/912,876.

(56) References Cited

OTHER PUBLICATIONS

All final and non-final office actions for U.S. Appl. No. 16/918,292.
All final and non-final office actions for U.S. Appl. No. 29/672,822.
All final and non-final office actions for U.S. Appl. No. 29/676,338.
All final and non-final office actions for U.S. Appl. No. 29/707,807.
All final and non-final office actions for U.S. Appl. No. 29/707,809.
All final and non-final office actions for U.S. Appl. No. 29/728,687.
All final and non-final office actions for U.S. Appl. No. 29/728,688.
All final and non-final Office Actions, U.S. Appl. No. 15/979,961.
All final and non-final Office Actions, U.S. Appl. No. 15/981,096.
All Office Actions, U.S. Appl. No. 17/070,205.
All Office Actions, U.S. Appl. No. 29/766,885.
Amerilab Technologies, Inc. (Minnesota, http://www.amerilabtech.comm/).
Anonymous "P8136 Poly(vinyl alcohol)" Internet article, [Online] XP002538935 retrieved from the Internet: URL:hllp/20NWW.sigmaaldrich.com/catalog/ProductDetail.do?D7=0%N25-SEARCH_CONCAT PNOIBRAND KEY%N4=P8136%7SCIAL%N25=0%QS=ON%F=SPEC retrieved on Jul. 28, 2009.
Briscoe et al. "The effects of hydrogen bonding upon the viscosity of aqueous poly( vinyl alcohol) solutions," from Polymer, 41 (2000), pp. 3851-3860.
Cardinal Health (Dublin, Ohio, http://spd.cardinal.com/).
Cima Labs, Inc. (Minnesota, http://www.cimalabs.com/).
Design of "Detergent tablets" (Design Registration No. 000634142-0003), (No. of Publicly known information: HH18274488), Registered Community Designs Bulletin, published by EUIPO on Jan. 9, 2007.
Design of "Detergent tablets" (Design Registration No. 000634142-0004), (No. of Publicly known information: HH18274489), Registered Community Designs Bulletin, published by EUIPO on Jan. 9, 2007.
Design of "Soaps" accepted on Jul. 11, 1986, Publishing Office: Korean Intellectual Property Office (KIPO), Document Name: Design Gazette (Application No. 3019850005996), Publication Date: Jun. 9, 1986, (No. of Publicly known information: HG21900612).
Dissolving Soap Strips (Ranir LLC, Michigan, www.ranir.com).
Encyclopedia of Polymer Science and Engineering, vol. 15, 2nd ed., pp. 204 308 Silicones, 1989.
Guerrini et al. "Thermal and Structural Characterization of Nanofibers of Poly( vinyl alcohol) Produced by Electrospinning", Journal of Applied Polymer Science, vol. 112, Feb. 9, 2009, pp. 1680-1687.
Hexagon 4 ward soap mold, Soap, Cosmetics, NEW Silicon mold, Published on Sep. 29, 2016, Retrieved from Internet : http://candlebox.com/product/%EC%9C%A1%EA%B0%81-4%EA%B5%AC-%EB%B9%84%EB%88%84%EB%AA%B0 %EB%93%9C/2206/?page_4=3#none.
Hildebrand, T., et al. "Quantification of bone microarchitecture with the structure mode index", Computer Methods in Biomechanics and Biomedical Engineering, vol. 1, Jan. 14, 1997, pp. 15-23.
How Gemz work?, Gemz Hair Care, published on Oct. 1, 2018, retrieved on Apr. 27, 2021, retrieved from the Internet URL: https://www.youtube.com/watch?v=ts1waYk43g4.
https ://www.craftcuts.com/hexagon-craft-shape. htmlHexagon wood cutouts, www.craftcuts.com, 1 page, reviewed as early as May 2018 (Year: 2018).
Japanese Paper Soap (http://www.wishingfish.com/papersoap.html).
Kuraray: "Mowiol—Technical data sheet", Jun. 1, 2010 (Jun. 1, 2010),pp. 1-4, XP055119891, Retrieved from the Internet: URL:http://www.kuraray.eu/fileadmin/Downloads/mowiol/TDS_Mowiol_en_20110624.pdf [retrieved on May 23, 2014].
Le Laboratoire du Bain (France, http://www.laboudubain.com/).
M.K. Industries (Gujarat India, http://www.soapstrips.com).
Megulars Car Wash Strips: Megulars Inc. California, http://www.automotivedigesl.com/view_art.asp?articles!D=12414.
Michelle Villett, Why You Need a Sulfate-Free Shampoo, The Skincare Edit, updated date: Jan. 25, 2019, Original publication date: Feb. 22, 2016 (Year: 2016), 7 pages.
MOVA Pharmaceutical and Kosmos (USA, http:/lwww.icon-pr.com/news/news/prinl.cfm?inv_id=256-1).
Okasaka et al., "Evaluation Of Anionic Surfactants Effects On The Skin Barrier Function Based On Skin Permeability", Pharmaceutical Development and Technology, vol. 24, No. 1, Jan. 23, 2018, pp. 99-104.
Product Review: Gemz Solid Shampoo, Travel As Much, published on Mar. 19, 2019, retrieved on Apr. 27, 2021, retrieved from the Internet URL: https://travelasmuch.com/gemz-solid-shampoo-review/.
Pure Soap Leafz: (Soap UNLTD. Netherlands, http://www.upandunder.com.uk/eshop/catalogue/testbs.asp?Manufacturer_ID=252&Activity_ID=33&Description_ID=157).
Sanipro Sanitary Products (Italy, http://www.sanipro.iit).
Solublon (Toyohashi Japan, http://www.solublon.com).
SPI Pharma (Delaware, http://www.spipharma.com).
Travelers Passport Paper Soap Sheets (http://www.weddingflavornow.com/index.asp?PageAction=VIEWPROD&PROD&ProdID=510).
Vaughan, C.D. "Solubility, Effects in Product, Package, Penetration and Preservation", Cosmetics and Toiletries, vol. 103, Oct. 1988.
Veslerby, A.: "Star Volume in Bone Research: A Histomorphometric Analysis Of Trabecular Bone Structure UsingVertical Sections", Anal Rec: Feb. 1993, 232(2), pp. 325-334.
Wenda (China, http://www.wenda.com).
Zhang et al. "Study on Morphology of Electrospun Poly( vinyl alcohol) Mats," European Polymer Journal 41 (2005), pp. 423-432.
U.S. Appl. No. 29/819,499, filed Dec. 15, 2021, Sharonda Lee Crawford Washington et al.
Definition of Derivative by Merriam Webster Online Dictionary, Year, 2021.
Wermuth et al. Drug Discovery, "Drug Discovery Today, 2006", vol. 11 7/8, 348-354, Year 2006.
Dow, UCARE™ Polymer LR-400, Technical Data Sheet, Downloaded in Mar. 2022, 4 pages.
Karen Duis et al, "Environmental fate and effects of water-soluble synthetic organic polymers used in cosmetic products", Environmental Sciences Europe, vol. 33, Article No. 21, Feb. 16, 2021, 78 pages.
U.S. Appl. No. 29/728,688, filed Mar. 20, 2020, Douglas Charles Cook et al.
U.S. Appl. No. 29/728,687, filed Mar. 20, 2020, Douglas Charles Cook et al.
U.S. Appl. No. 29/707,809, filed Oct. 1, 2019, Sharonda Lee Crawford Washington et al.
U.S. Appl. No. 29/707807, filed Oct. 1, 2019, Sharonda Lee Crawford Washington et al.
U.S. Appl. No. 29/766,885, filed Jan. 19, 2021, Wee Hau Tan et al.
PCT International Search Report and Written Opinion for PCT/CN2019/119586 dated Aug. 26, 2020.
"Green Chemistry", Huazhong University of Science and Technology Press, published on Jun. 30, 2008, pp. 6.
Ni Genshan et al. "Drug Classification and Pharmacology Summary", PLA Press, published on Apr. 30, 1988, pp. 3.
All Office Actions; U.S. Appl. No. 12/633,228, filed Dec. 8, 2009.
All Office Actions; U.S. Appl. No. 12/633,257, filed Dec. 8, 2009.
All Office Actions; U.S. Appl. No. 12/633,301, filed Dec. 8, 2009.
All Office Actions; U.S. Appl. No. 12/633,335, filed Dec. 8, 2009.
All Office Actions; U.S. Appl. No. 12/633,415, filed Dec. 8, 2009.
All Office Actions; U.S. Appl. No. 12/633,550, filed Dec. 8, 2009.
All Office Actions; U.S. Appl. No. 13/561,298, filed Jul. 30, 2012.
All Office Actions; U.S. Appl. No. 13/915,797, filed Jun. 12, 2013.
Hiroshi Yagi & 4 Others, Research Study of a Frictionprotector for Preventing a Tow Line From Breaking,Working Papers for Fiscal 2006 | Japan | Japan Coast Guard Dec. 2007, pp. 1-8.
Latorre Carmen,Nanotribological Effects of Hair Careproducts and Environment On Human Hair Using Atomic Forcemicroscopy,Journal of Vacuum Science and Technology:Part A, U. S . A, AVS / AI P , Jun. 28, 2005, V2 3 N 4 , p. 10 3 4-lO4 5.

\* cited by examiner

POROUS DISSOLVABLE SOLID STRUCTURE

FIELD OF THE INVENTION

The present application is directed to porous dissolvable solid structures containing non-sulfate surfactants.

BACKGROUND OF THE INVENTION

Porous dissolvable solid structures comprising surfactant(s) and/or other active ingredients in a water-soluble polymeric carrier or matrix can be used for cleansing. Such sheets are particularly useful for delivering surfactants and/or other active ingredients upon dissolution in water. In comparison with traditional granular or liquid forms in the same product category, such structures have better structural integrity, are more concentrated and easier to store, ship/transport, carry, and handle. There has been a recent push for cleansers which are free from sulfate. Sulfate based cleansers, however, are traditionally used in dissolvable solid structures and the removal of them can create structures which are difficult to process. As such, there is a need for a sulfate free dissolvable solid structure which is processable.

SUMMARY OF THE INVENTION

In one aspect, the present application is directed to a porous dissolvable solid structure, comprising: a) from about 20% to about 50%, preferably from about 20% to about 50%, more preferably from about 28% to about 45%, even more preferably from about 34% to about 41% by weight of the porous dissolvable solid of an isethionate surfactant, preferably sodium cocoyl isethionate, sodium lauroyl methyl isethionate, or a combination thereof; b) from about 4% to about 20%, preferably from about 6% to about 18%, more preferably from about 8% to about 16%; even more preferably from about 10% to about 16%, by weight of the porous dissolvable solid of a non-sulfate anionic surfactant, preferably sodium cocoyl glutamate, sodium lauroyl glutamate, disodium laureth sulfosuccinate, or a combination thereof; c) from about 5% to about 28%, preferably from about 7% to about 26%, more preferably from about 9% to about 24%; even more preferably from about 11% to about 22%, by weight of the solid structure of an amphoteric surfactant, zwitterionic surfactant or combination thereof; preferably lauramidopropyl betaine, cocamidopropyl betaine, sodium lauroamphoacetate, or a combination thereof; d) from about 18% to about 38%, preferably from about 20% to about 36%, more preferably from about 22% to about 34%; even more preferably from about 24% to about 32%, by weight of the porous dissolvable solid structure of polyvinyl alcohol; and e) from about 4.5% to about 20%, preferably from about 5.5% to about 17%, more preferably from about 6.5% to about 14%, even more preferably from about 7.5% to about 11% of glycerin; wherein said porous dissolvable solid structure has a density of from about 0.05 g/cm$^3$ to about 0.20 g/cm$^3$, preferably from about 0.07 g/cm$^3$ to about 0.18 g/cm$^3$, more preferably from about 0.09 g/cm$^3$ to about 0.16 g/cm$^3$, or even more preferably from about 0.11 g/cm$^3$ to about 0.14 g/cm$^3$.

These and other aspects will become more apparent upon reading the following detailed description.

DETAILED DESCRIPTION

Definitions

The term "flexible" as used herein refers to the ability of an article to withstand stress without breakage or significant fracture when it is bent at 90° along a center line perpendicular to its longitudinal direction. Preferably, such article can undergo significant elastic deformation and is characterized by a Young's Modulus of no more than 5 GPa, preferably no more than 1 GPa, more preferably no more than 0.5 GPa, most preferably no more than 0.2 GPa.

The term "solid" as used herein refers to the ability of an article to substantially retain its shape (i.e., without any visible change in its shape) at 20° C. and under the atmospheric pressure, when it is not confined and when no external force is applied thereto.

Porous dissolvable solid structures can be made by first preparing a pre-mixture containing various materials, then aerating the pre-mixture by introducing a gas thereunto, followed by forming the aerated pre-mixture into a sheet, and finally drying the sheet at an elevated temperature. The porous dissolvable solid structures are formed during the drying step under simultaneous mechanisms of water evaporation, bubble collapse, interstitial liquid drainage from the thin film bubble facings into the plateau borders between the bubbles (which generates openings between the bubbles and forms the open cells), and solidification of the pre-mixture. Various processing conditions may influence these mechanisms, e.g., solid content in the wet pre-mixture, viscosity of the wet pre-mixture, gravity, and the drying temperature, and the need to balance such processing conditions so as to achieve controlled drainage and form the desired porous dissolvable solid structures.

Here is an example of a manufacturing process for a porous dissolvable solid structure. A feeding trough is filled with an aerated wet pre-mixture. A heated rotatable cylinder (also referred to as a drum dryer) is placed above said feeding trough. Said heated drum dryer has a cylindrical heated outer surface characterized by a controlled surface temperature of about 130° C., and it rotates along a clockwise direction (as shown by the thin curved line with an arrowhead) to pick up the aerated wet pre-mixture from the feeding trough. The aerated wet pre-mixture forms a thin sheet over the cylindrical heated outer surface of the drum dryer, which rotates and dries such sheet of aerated wet pre-mixture in approximately 10-15 minutes to form a porous solid structure. A leveling blade may be placed near the pre-mixture pick-up location to ensure a consistent thickness of the sheet so formed, although it is possible to control the thickness of the sheet simply by modulating the viscosity of the aerated wet pre-mixture and the rotating speed and surface temperature of the drum dryer. Once dried, the porous solid structure can then picked up, either manually or by a scraper at the end of the drum rotation. The sheet of porous solid structures can be rolled into a roll awaiting further processing.

The wet pre-mixture goes through a pretty rigorous process in the course of becoming a porous solid structure and the completed porous solid structure can be subjected to additional processing to be formed into a consumer friendly product. Thus, the ability to process both the pre-mixture to form a porous solid structure and the formed porous solid structure are important. When sulfate based surfactants were removed from pre-mixture formulations, there were issues processing these formulations into both porous solid structures and during processing after the formation of the porous solid structures. These issues can include, for example, peel-ability, roll-ability, and strength during roll unwinding and cutting.

In evaluating initial non-sulfate formulations, it is discovered that there were some issues with processability. It is believed that non-sulfate formulations can be prone to poor tensile properties making the per-mixture and/or resulting porous solid structure difficult to process and commercialize. The tensile property of Strain at Break has been found to correlate to the processability and scale-up of the formulations and in particular peel-ability, roll-ability and strength during roll unwinding & slitting/cutting. Particularly, a strain at break of 20 mm or more tends to predict a product which will be sufficiently processable. Thus the strain at break of a porous dissolvable structure can be, for example, 20 mm or more, 30 mm or more, or 35 mm or more.

Surprisingly, the present inventors have discovered that porous dissolvable solid structures comprising a high level of isethionate based surfactants (20% or more by weight of the porous dissolvable solid) as primary surfactants in combination with a secondary anionic co-surfactant and an amphoteric/zwitterionic surfactant provide step-changed tensile strength to solve the heretofore mentioned processing challenges, while still providing fast dissolution properties under consumer relevant conditions. While not being bound to theory, it is hypothesized that a balancing of the crystallinity of the isethionate surfactants by modulating it to a sufficient degree (to enable cell opening after aeration during the drying process and high elasticity & tensile strength) with the secondary anionic cosurfactant(s) and amphoteric/zwitterionic surfactant(s) allows for the formation of an acceptable porous dissolvable solid structure.

The balancing of the surfactant cocktail, however, took some work. As can be seen in Table 1 below, several porous solid structures which contain varying levels of similar surfactants (the exact formulations are below in the Examples Section) have vastly differing Strain at Break values. A Strain at Break value of 20 mm or more is believed to signify a porous dissolvable solid structure which will be adequately processable. Thus, the examples numbered 14 and 20-24 have an unacceptable strain at break.

TABLE 1

| Example # | % Isethionate surfactants | % Anionic Co-Surfactants | % Amphoteric/ Zwitterionic Surfactants | Strain at Break (mm) |
|---|---|---|---|---|
| 13 | 39.6% | 7.9% | 15.8% | 40.6 |
| 15 | 39.6% | 15.8% | 7.9% | 44.9 |
| 16 | 39.6% | 15.8% | 7.9% | 53.1 |
| 17 | 23.7% | 23.7% | 15.8% | 29.3 |
| 18 | 23.7% | 15.8% | 23.7% | 35.6 |
| 19 | 23.7% | 15.8% | 23.7% | 24.6 |
| 14 | 23.7% | 7.9% | 31.6% | 15.4 |
| 20 | 39.5% | 0.0% | 23.7% | 15.0 |
| 21 | 20.6% | 8.8% | 29.5% | 16.5 |
| 22 | 17.7% | 0.0% | 41.3% | 15.3 |
| 23 | 17.7% | 0.0% | 41.3% | 10.6 |
| 24 | 8.8% | 8.8% | 41.3% | 8.7 |

Pre-Mixture

As noted above, a porous dissolvable solid structure starts as a pre-mixture. A pre-mixture is generally prepared by mixing of the desired ingredients. Ingredients for a porous dissolvable solid structure can include, for example, surfactants, water-soluble polymers, plasticizers, water, etc. These will be discussed more fully below. The pre-mixture can be formed using a mechanical mixer. Mechanical mixers useful herein, include, but aren't limited to pitched blade turbines or MAXBLEND™ mixer (Sumitomo Heavy Industries).

The viscosity of the pre-mixture can be adjusted for optimum processability. It can be, for example, in the range of about 1,000 cps to about 25,000 cps when measured at 40° C. and 1 s$^{-1}$. Viscosity of the pre-mixture can have a significant impact on the pore expansion and pore opening of the aerated pre-mixture during the subsequent drying step, and pre-mixtures with different viscosities may form flexible, porous, dissolvable solid sheet articles of very different foam structures. On one hand, when the pre-mixture is has a viscosity higher than about 25,000 cps aeration of such wet pre-mixture may become more difficult. More importantly, interstitial liquid drainage from thin film bubble facings into the plateau borders of the three-dimensional foam during the subsequent drying step may be adversely affected or significantly limited. The interstitial liquid drainage during drying impacts pore expansion and pore opening in the aerated wet pre-mixture during the subsequent drying step. As a result, the flexible, porous, dissolvable solid sheet article so formed thereby may have significantly smaller pores and less interconnectivity between the pores (i.e., more "closed" pores than open pores), which render it harder for water to ingress into and egress from such sheet article. On the other hand, when the pre-mixture has a viscosity lower than about 1,000 cps the aerated pre-mixture may not be sufficiently stable, i.e., the air bubbles may rupture, collapse, or coalescence too quickly in the wet pre-mixture after aeration and before drying. Consequently, the resulting solid sheet article may be much less porous and more dense than desired.

Thus, viscosity of the pre-mixture may range, for example, from about 1,000 cps to about 25,000 cps, from about 3,000 cps to about 24,000 cps, from about 5,000 cps to about 23,000 cps, or from about 10,000 cps to about 20,000 cps, as measured at 40° C. and 1 sec$^{-1}$. The pre-mixture viscosity values can be measured using a Malvern Kinexus Lab+ rheometer with cone and plate geometry (CP1/50 SR3468 SS), a gap width of 0.054 mm, a temperature of 40° C. and a shear rate of 1.0 reciprocal seconds for a period of 360 seconds.

The level of solids in the pre-mixture can also impact processability. The level of solids in the pre-mixture can be, for example, from about 15% to about 70%, from about 20% to about 50%, or from about 25% to about 45% by total weight of said wet pre-mixture. The percent solid content is the summation of the weight percentages by weight of the total processing mixture of all solid components, semi-solid components and liquid components excluding water and any obviously volatile materials such as low boiling alcohols.

The wet pre-mixture can be pre-heated immediately prior to and/or during the aeration process at above ambient temperature but below any temperatures that would cause degradation of the components therein. For example, the wet pre-mixture can be kept at an elevated temperature ranging from about 40° C. to about 100° C., from about 50° C. to about 95° C., from about 60° C. to about 90° C., or from about 75° C. to about 85° C. Further, additional heat can be applied during the aeration process to try and maintain the pre-mixture at such an elevated temperature as was attained prior to aeration. This can be accomplished, for example, via conductive heating from one or more surfaces, injection of steam or other processing means.

It is believed that the act of pre-heating the wet pre-mixture before and/or during the aeration step may provide a means for lowering the viscosity of pre-mixtures comprising higher percent solids content for improved introduction of bubbles into the mixture and formation of the desired solid sheet article. Achieving higher percent solids content is desirable since it may reduce the overall energy requirements for drying. The increase of percent solids may therefore conversely lead to a decrease in water level content and an increase in viscosity. As mentioned hereinabove, pre-mixtures with viscosities that are too high are undesirable.

Pre-heating may effectively counteract such viscosity increase and thus allow for the manufacture of a fast dissolving sheet article even when using high solid content pre-mixtures.

The pre-mixture may also be aerated. Aeration of the wet pre-mixture is conducted in order to introduce a sufficient amount of air bubbles into the wet pre-mixture for subsequent formation of the porous dissolvable solid structures therein upon drying. Once sufficiently aerated, the pre-mixture is characterized by a density that is lower than that of the non-aerated pre-mixture (which may contain a few inadvertently trapped air bubbles) or an insufficiently aerated wet pre-mixture (which may contain some bubbles but at a much lower volume percentage and of significantly larger bubble sizes). The aerated wet pre-mixture has a density ranging, for example, from about 0.05 g/ml to about 0.5 g/ml, from about 0.08 g/ml to about 0.4 g/ml, from about 0.1 g/ml to about 0.35 g/ml, from about 0.15 g/ml to about 0.3 g/ml, or from about 0.2 g/ml to about 0.25 g/ml.

Aeration can be accomplished by either physical or chemical means. For example, it can be accomplished by introducing a gas into the pre-mixture through mechanical agitation, for example, by using any suitable mechanical processing means, including but not limited to: a rotor stator mixer, a planetary mixer, a pressurized mixer, a non-pressurized mixer, a batch mixer, a continuous mixer, a semi-continuous mixer, a high shear mixer, a low shear mixer, a submerged sparger, or any combinations thereof. It may be achieved via chemical means, for example, by using chemical forming agents to provide in-situ gas formation via chemical reaction of one or more ingredients, including formation of carbon dioxide ($CO_2$ gas) by an effervescent system.

Bubble size of the aerated pre-mixture assists in achieving uniform layers in the porous dissolvable solid structures of the resulting solid sheet article. The bubble size of the aerated pre-mixture can be, for example, from about 5 to about 100 microns or from about 20 microns to about 80 microns. Uniformity of the bubble sizes causes the resulting porous dissolvable solid structures to have consistent densities.

Sheet Formation

After sufficient aeration, the aerated pre-mixture can form one or more sheets with opposing first and second sides. The sheet-forming step can be conducted in any suitable manner, e.g., by extrusion, casting, molding, vacuum-forming, pressing, printing, coating, and the like. More specifically, the aerated pre-mixture can be formed into a sheet by: (i) casting it into shallow cavities or trays or specially designed sheet moulds; (ii) extruding it onto a continuous belt or screen of a dryer; (iii) coating it onto the outer surface of a rotary drum dryer. The supporting surface upon which the sheet is formed can be formed by or coated with materials that are anti-corrosion, non-interacting and/or non-sticking, such as metal (e.g., steel, chromium, and the like), TEFLON®, polycarbonate, NEOPRENE®, HDPE, LDPE, rubber, glass and the like. Examples of suitable manufacturing methods can be found, for example, in CN 2019/071751; WO2012138820; and WO2010077627 all of which are incorporated herein by reference.

The formed sheet of aerated wet pre-mixture, i.e. a porous solid dissolvable structure, can have a thickness ranging, for example, from 0.5 mm to 4 mm, from 0.6 mm to 3.5 mm, from 0.7 mm to 3 mm, from 0.8 mm to 2 mm, or from 0.9 mm to 1.5 mm Controlling the thickness of such formed sheet of aerated pre-mixture may be important for ensuring that the resulting solid sheet article has the desired open celled structure. If the formed sheet is too thin (e.g., less than 0.5 mm in thickness), many of the air bubbles trapped in the aerated pre-mixture will expand during the subsequent drying step to form through-holes that extend through the entire thickness of the resulting solid sheet article. Such through-holes, if too many, may significantly compromise both the overall structural integrity and aesthetic appearance of the sheet article. If the formed sheet is too thick, not only it will take longer to dry, but also it will result in a solid sheet article with greater pore size variations between different regions (e.g., top, middle, and bottom regions) along its thickness. The longer the drying time, the more imbalance of forces may occur through bubble rupture/collapse/coalescence, liquid drainage, pore expansion, pore opening, water evaporation, and the like. Further, multiple layers of relatively thin sheets can be assembled into three-dimensional structures of greater thickness to deliver the desired cleaning benefits or other benefits, while still providing satisfactory pore structures for fast dissolution as well as ensuring efficient drying within a relatively short drying time.

Drying

The porous dissolvable solid structure may be dried in any manner appropriate in the art. During drying, the process may include the use of an antigravity heating direction either through the entire drying time or at least half of the drying time. Without being bound by any theory, it is believed that such anti-gravity heating direction may reduce or counteract excessive interstitial liquid drainage toward the bottom region of the formed sheet during the drying step. Further, because the top surface is dried last, it allows longer time for air bubbles near the top surface of the formed sheet to expand and form pore openings on the top surface (because once the wet matrix is dried, the air bubbles can no longer expand or form surface openings). Consequently, the porous dissolvable solid structure formed by drying with such anti-gravity heating is characterized by improved open cell structures that can enable faster dissolution as well as other unexpected benefits. The antigravity heating may be provided, for example, by a rotary drum, conduction based heating arrangement, etc.

The drying process may also include the use of a heated rotatable cylinder. The heated rotatable cylinder, often used in drum drying, can be heated internally, e.g., by steam or electricity, and can be rotated, for example, by a motorized drive installed on a base bracket at a predetermined rotational speed. The heated rotatable cylinder or drum can have an outer diameter ranging, for example, from about 0.5 meters to about 10 meters, from about 1 meter to about 5 meters, or from about 1.5 meters to about 2 meters. It may have a controlled surface temperature, for example, of from about 80° C. to about 170° C., from about 90° C. to about 150° C., or from about 100° C. to about 140° C. Further, such heated rotatable cylinder can be rotating at a speed, for example, of from about 0.005 rpm to about 0.25 rpm, from about 0.05 rpm to about 0.2 rpm, or from about 0.1 rpm to about 0.18 rpm.

Said heated rotatable cylinder can be coated with a non-stick coating on its outer surface. The non-stick coating may be overlying on the outer surface of the heated rotatable drum, or it can be fixed to a medium of the outer surface of the heated rotatable drum. The medium includes, but is not limited to, heat-resisting non-woven fabrics, heat-resisting carbon fiber, heat-resisting metal or non-metallic mesh and the like. The non-stick coating can effectively preserve structural integrity of the sheet-like article from damage during the sheet-forming process.

There can also be provided a feeding mechanism for adding the aerated pre-mixture of raw materials as described hereinabove onto the heated rotatable drum, thereby forming a thin layer of the viscous pre-mixture onto the outer surface of the heated rotatable drum. Such thin layer of the pre-mixture is therefore dried by the heated rotatable drum via contact-heating/drying. The feeding mechanism can include, for example, a feeding trough, while said feeding trough has installed thereupon at least one or more feeding hoppers, an imaging device for dynamic observation of the feeding, and an adjustment device for adjusting the position and inclination angle of the feeding hopper. By using said adjustment device to adjust the distance between said feeding hopper and the outer surface of the heated rotatable drum, the need for different thicknesses of the formed sheet-like article can be met. The adjustment device can also be used to adjust the feeding hopper to different inclination angles so as to meet the material requirements of speed and quality.

There may also be a static scraping mechanism for scraping or scooping up the porous dissolvable solid structure already formed by the heated rotatable drum. The static scraping mechanism can be installed, for example, on the base bracket, or on one side thereof, for transporting the already formed porous dissolvable solid structure downstream for further processing. The static scraping mechanism can automatically or manually move close and go away from the heated rotatable drum.

The making process of the porous, dissolvable solid structure article can be as follows. Firstly, the heated rotatable drum with the non-stick coating on the base bracket is driven by the motorized drive. Next, the adjustment device adjusts the feeding mechanism so that the distance between the feeding hopper and the outer surface of the heated rotatable drum reaches a preset value. Meanwhile, the feeding hopper adds the aerated pre-mixture containing all or some raw materials for making the porous dissolvable solid structure onto an outer surface of the heated rotatable drum, to form a thin layer of said aerated pre-mixture thereon with the desired thickness. Optionally, a suction device of the heating shield sucks the hot steam generated by the heated rotatable drum. Next, the static scraping mechanism scrapes/scoops up a dried/solidified sheet article, which is formed by the thin layer of aerated wet pre-mixture after it is dried by the heated rotatable drum at a relatively low temperature (e.g., 130° C.). The dried/solidified sheet article can also be manually or automatically peeled off, without such static scraping mechanism and then rolled up by a roller bar.

The total drying time depends on the formulations and solid contents in the pre-mixture, the drying temperature, the thermal energy influx, and the thickness of the porous dissolvable solid structure to be dried. The drying time can be, for example, from about 1 minute to about 60 minutes, from about 2 minutes to about 30 minutes, from about 2 to about 15 minutes, from about 2 to about 10 minutes, or from about 2 to about 5 minutes.

During such drying time, the heating direction can be so arranged that it is substantially opposite to the gravitational direction for more than half of the drying time, for more than 55% or 60% of the drying time (e.g., as in the rotary drum-based heating/drying arrangement described hereinabove), or for more than 75% or even 100% of the drying time (e.g., as in a bottom conduction-based heating/drying arrangement). Further, the sheet of aerated wet pre-mixture can be dried under a first heating direction for a first duration and then under a second, opposite heating direction under a second duration, while the first heating direction is substantially opposite to the gravitational direction. Such change in heating direction can be readily achieved by various other arrangements not illustrated herein, e.g., by an elongated heated belt of a serpentine shape that can rotate along a longitudinal central axis.

The porous dissolvable solid sheet article may further be characterized by one or more of the following:
- a Percent Open Cell Content of from about 85% to 100% or from about 90% to 100%;
- an Overall Average Pore Size of from about 150 µm to about 1000 µm, or from about 200 µm to about 600 µm;
- an Average Cell Wall Thickness of from about 5 µm to about 200 µm, from about 10 µm to about 100 µm, or from about 10 µm to about 80 µm;
- a final moisture content of from about 0.5% to about 25%, from about 1% to about 20%, or from about 3% to about 10%, by weight of said porous dissolvable solid structure;
- a thickness ranging from about 0.6 mm to about 3.5 mm, from about 0.7 mm to about 3 mm, from about 0.8 mm to about 2 mm, or from about 1 mm to about 1.5 mm;
- a basis weight of from about 50 grams/m$^2$ to about 250 grams/m$^2$, from about 80 grams/m$^2$ to about 220 grams/m$^2$, or from about 100 grams/m$^2$ to about 200 grams/m$^2$;
- a density of from about 0.05 grams/cm$^3$ to about 0.5 grams/cm$^3$, from about 0.06 grams/cm$^3$ to about 0.4 grams/cm$^3$, from about 0.07 grams/cm$^3$ to about 0.2 grams/cm$^3$, or from about 0.08 grams/cm$^3$ to about 0.15 grams/cm$^3$; and
- a Specific Surface Area of about 0.03 m$^2$/g to about 0.25 m$^2$/g, from about 0.04 m$^2$/g to 0.22 m$^2$/g, from about 0.05 m$^2$/g to about 0.2 m$^2$/g, or from about 0.1 m$^2$/g to about 0.18 m$^2$/g.

Formulations

A porous dissolvable solid structure as described herein may contain, for example, surfactant, water soluble polymer, plasticizer, additives, etc. A porous dissolvable solid structure may comprise, for example, from about 25% to about 80%, from about 40% to about 70%, total surfactant, by weight of the porous dissolvable solid structure. It may also comprise from about 10% to about 40% of water soluble polymer, by weight of the porous dissolvable solid structure. A porous dissolvable structure may also comprise multiple layers. These layers can be made up of, for example, single layers of porous dissolvable solid structures. The single layer porous dissolvable structures can be in any applicable form, like a sheet, for example. The porous dissolvable structure may also be flexible. Porous dissolvable solid structures may be used, for example, as a skin cleanser. The porous dissolvable solid structure can be an open cell foam.

Surfactant

The surfactants may function as emulsifying agents during the aeration process to create a sufficient amount of stable bubbles for forming the desired open cell structure. The surfactants may also function as active ingredients for delivering a desired cleansing benefit. A porous dissolvable solid structure can comprise, for example, an isethionate surfactant, a non-sulfate anionic surfactant, an amphoteric surfactant, a zwitterionic surfactant, or a combination of amphoteric and zwitterionic surfactants.

The isethionate surfactant may be present at a level of about 20% to about 50%, about 22% to about 50%, about 28% to about 45%, from about 31% to about 41%, from about 34% to about 41%, from about 38% to about 41%, from about 20% to about 30%, from about 21% to about 25%, by weight of the porous dissolvable solid. The isethionate surfactant can include, for example, sodium cocoyl isethionate, sodium lauroyl methyl isethionate, or a combination thereof. In one example, a porous dissolvable solid structure comprises from about 15% to about 32%, by weight, of sodium lauroyl methyl isethionate; and from about 7% to about 25%, by weight, of sodium cocoyl isethionate. In another example, a porous dissolvable solid structure comprises from about 21% to about 25%, by weight, of sodium cocoyl isethionate.

The non-sulfate anionic surfactant includes anionic surfactants which are free of sulfate. The non-sulfate anionic surfactant may be present at a level of about 4% to about 25%, about 6% to about 18%, about 7% to about 18%, about 7% to about 17%, about 8% to about 16%; about 10% to about 16%, about 14% to about 17%, from about 15% to about 25%, or from about 22% to about 25%, by weight of the porous dissolvable solid structure. The non-sulfate anionic surfactant may include sodium lauroyl sarcosinate, lauryl sarcosine, cocoyl sarcosine, sodium lauroyl glutamate, sodium cocoyl glutamate, disodium lauryl sulfosuccinate, disodium laureth sulfosuccinate, sodium cocoyl taurate, sodium lauroyl taurate, sodium lauroyl lactylate, sodium cocoyl lactylate, sodium lauroyl glycinate, sodium cocoyl glycinate, and combinations thereof. A subset of the non-sulfate anionic surfactant can include, for example, sodium cocoyl glutamate, sodium lauroyl glutamate, disodium laureth sulfosuccinate, or a combination thereof.

The amphoteric and/or zwitterionic surfactant may be present at a level of about 5% to about 28%, about 7% to about 26%, about 9% to about 24%; about 11% to about 22%, about 7% to about 18%, about 7% to about 17%, about 14% to about 17%, about 15% to about 25%, or about 22% to about 25%, by weight of the porous solid structure Amphoteric co-surfactants suitable for use herein can include those surfactants described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable amphoteric surfactant include, but are not limited to, those selected from the group consisting of: sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethyl-7 carboxyamphodiacetate, lauraminopropionic acid, lauroamphodipropionic acid, lauryl aminopropylglycine, lauryl diethylenediaminoglycine, and mixtures thereof.

The amphoteric co-surfactant can be a surfactant according to the following structure:

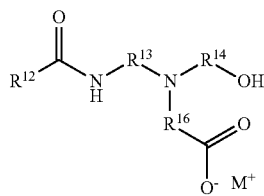

wherein $R^{12}$ is a C-linked monovalent substituent selected from the group consisting of substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; $R^{13}$, $R^{14}$, and $R^{15}$ are each independently selected from the group consisting of C-linked divalent straight alkyl systems comprising 1 to 3 carbon atoms, and C-linked divalent branched alkyl systems comprising 1 to 3 carbon atoms; and M+ is a monovalent counterion selected from the group consisting of sodium, ammonium and protonated triethanolamine One subset of suitable amphoteric surfactants includes sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, triethanolamine cocoamphoacetate, and mixtures thereof.

The porous dissolvable solid structure may comprise a zwitterionic surfactant, wherein the zwitterionic surfactant is a derivative of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. The zwitterionic surfactant can be selected from the group consisting of: cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and mixtures thereof. A suitable zwitterionic surfactant is lauryl hydroxysultaine. The zwitterionic surfactant can be selected from the group consisting of: lauryl hydroxysultaine, cocamidopropyl hydroxysultaine, coco-betaine, coco-hydroxysultaine, coco-sultaine, lauryl betaine, lauryl sultaine, and mixtures thereof.

A subset of the amphoteric and/or zwitterionic surfactants can include, for example, lauramidopropyl betaine, cocamidopropyl betaine, sodium lauroamphoacetate, sodium cocoamphoacetate, or a combination thereof.

Water soluble polymer A porous dissolvable solid structure may include a water soluble polymer in an amount ranging, for example, from about 18% to about 38%, from about 22% to about 34%, or from about 24% to about 32%, by weight of the porous dissolvable solid structure.

Water-soluble polymers suitable herein may be selected, for example, from those with weight average molecular weights ranging from about 50,000 to about 400,000 Daltons, from about 60,000 to about 300,000 Daltons, from about 70,000 to about 200,000 Daltons, or from about 80,000 to about 150,000 Daltons. The weight average molecular weight is computed by summing the average molecular weights of each polymer raw material multiplied by their respective relative weight percentages by weight of the total weight of polymers present within the porous dissolvable solid structure. The weight average molecular weight of the water-soluble polymer used herein may impact the viscosity of the wet pre-mixture, which may in turn influence the bubble number and size during the aeration step as well as the pore expansion/opening results during the drying step. Further, the weight average molecular weight of the water-soluble polymer may affect the overall film-forming properties of the wet pre-mixture and its compatibility/incompatibility with certain surfactants.

The water-soluble polymers useful herein may include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, copolymers of acrylic acid and methyl acrylate, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrrolidone/vinyl acetate copolymers, copolymers of anionic, cationic and amphoteric monomers, and combinations thereof.

The water-soluble polymers may also be selected from naturally sourced polymers including those of plant origin, examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers can also be used as water-soluble polymers. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

The water-soluble polymer may also include starch. As used herein, the term "starch" includes both naturally occurring and modified starches. Typical natural sources for starches can include cereals, tubers, roots, legumes and fruits. More specific natural sources can include corn, pea, potato, banana, barley, wheat, rice, sago, amaranth, tapioca, arrowroot, canna, sorghum, and waxy or high amylase varieties thereof. The natural starches can be modified by any modification method known in the art to form modified starches, including physically modified starches, such as sheared starches or thermally-inhibited starches; chemically modified starches, such as those which have been cross-linked, acetylated, and organically esterified, hydroxyethylated, and hydroxypropylated, phosphorylated, and inorganically esterified, cationic, anionic, nonionic, amphoteric and zwitterionic, and succinate and substituted succinate derivatives thereof; conversion products derived from any of the starches, including fluidity or thin-boiling starches prepared by oxidation, enzyme conversion, acid hydrolysis, heat or acid dextrinization, thermal and or sheared products may also be useful herein; and pregelatinized starches which are known in the art.

A useful subset of water soluble polymers can include polyvinyl alcohols, polyvinylpyrrolidones, polyalkylene oxides, starch and starch derivatives, pullulan, gelatin, hydroxypropylmethylcelluloses, methycelluloses, carboxymethycelluloses or combinations thereof. An even further subset includes polyvinyl alcohols, hydroxypropylmethylcelluloses, or a combination thereof.

Polyvinyl alcohols useful herein can include those characterized by a degree of hydrolysis ranging from about 40% to about 100%, from about 50% to about 95%, from about 70% to about 92%, or from about 80% to about 90%. Commercially available polyvinyl alcohols can include those from Celanese Corporation (Texas, USA) under the SELVOL™ trade name including, but not limited to, SELVOL™ 523, SELVOL™ 530, SELVOL™ 540, SELVOL™ 518, SELVOL™ 513, SELVOL™ 508, SELVOL™ 504; those from Kuraray Europe GmbH (Frankfurt, Germany) under the Mowiol® and POVAL™ trade names; and PVA 1788 (also referred to as PVA BP17) commercially available from various suppliers including Lubon Vinylon Co. (Nanjing, China); and combinations thereof. A porous dissolvable solid structure can include, for example, from about 10% to about 25%, or about 15% to about 23%, by total weight of such article, of a polyvinyl alcohol having a weight average molecular weight ranging from 80,000 to about 150,000 Daltons and a degree of hydrolysis ranging from about 80% to about 90%.

A single starch or a combination of starches may be used as a filler material in such an amount as to reduce the overall level of water-soluble polymers required, so long as it helps provide the sporous dissolvable solid structure with the requisite structure and physical/chemical characteristics as described herein. However, too much starch may comprise the solubility and structural integrity of the sheet article. Starch may be present, for example, at a level of no more 20%, from 0% to about 10%, from 0% to 5%, or from 0% to 1%, by weight of said porous dissolvable solid structure, of starch.

Plasticizers

Plasticizers may be present in the porous dissolvable solid structure at an amount ranging from about 4.5% to about 20%, from about 5.5% to about 17%, from about 6.5% to about 14%, from 7.5% to 11%, by total weight of said porous dissolvable solid structure. Suitable plasticizers for use herein can include, for example, polyols, copolyols, polycarboxylic acids, polyesters, dimethicone copolyols, and combinations thereof.

Examples of useful polyols include, but are not limited to: glycerin, diglycerin, ethylene glycol, polyethylene glycol (especially 200-600), propylene glycol, butylene glycol, pentylene glycol, glycerol derivatives (such as propoxylated glycerol), glycidol, cyclohexane dimethanol, hexanediol, 2,2,4-trimethylpentane-1,3-diol, pentaerythritol, urea, sugar alcohols (such as sorbitol, mannitol, lactitol, xylitol, maltitol, and other mono- and polyhydric alcohols), mono-, di- and oligo-saccharides (such as fructose, glucose, sucrose, maltose, lactose, high fructose corn syrup solids, and dextrins), ascorbic acid, sorbates, ethylene bisformamide, amino acids, and combinations thereof.

Examples of polycarboxylic acids include, but are not limited to citric acid, maleic acid, succinic acid, polyacrylic acid, polymaleic acid, and combinations thereof.

Examples of suitable polyesters include, but are not limited to, glycerol triacetate, acetylated-monoglyceride, diethyl phthalate, triethyl citrate, tributyl citrate, acetyl triethyl citrate, acetyl tributyl citrate, and combinations thereof.

Examples of suitable dimethicone copolyols include, but are not limited to, PEG-12 dimethicone, PEG/PPG-18/18 dimethicone, PPG-12 dimethicone, and combinations thereof.

Other suitable plasticizers include, but are not limited to, alkyl and allyl phthalates; napthalates; lactates (e.g., sodium, ammonium and potassium salts); sorbeth-30; urea; lactic acid; sodium pyrrolidone carboxylic acid (PCA); sodium hyraluronate or hyaluronic acid; soluble collagen; modified protein; monosodium L-glutamate; alpha & beta hydroxyl acids such as glycolic acid, lactic acid, citric acid, maleic acid and salicylic acid; glyceryl polymethacrylate; polymeric plasticizers such as polyquaterniums; proteins and amino acids such as glutamic acid, aspartic acid, and lysine; hydrogen starch hydrolysates; other low molecular weight esters (e.g., esters of $C_2$-$C_{10}$ alcohols and acids); and any other water soluble plasticizer known to one skilled in the art of the foods and plastics industries; and mixtures thereof.

A useful subset of plasticizers includes glycerin, ethylene glycol, polyethylene glycol, propylene glycol, and mixtures thereof. Herein, glycerin is the most commonly used plasticizer.

Additional Ingredients

In addition to the above-described ingredients, e.g., the water-soluble polymer, the surfactant(s) and the plasticizer, the porous dissolvable solid structure may comprise one or more additional ingredients, depending on its intended application. Such one or more additional ingredients may include, for example personal cleansing actives. Such ingredients may also work to help with the formulation and or aesthetics of the porous dissolvable solid structure, for example, pH modifiers, colorants, perfumes, etc.

The porous dissolvable solid structure may further comprise other optional ingredients that are known for use or otherwise useful in porous dissolvable solid structure, provided that such optional materials are compatible with the selected essential materials described herein, or do not otherwise unduly impair product performance.

Multi-layer Porous Dissolvable Solid Structures

Once the porous dissolvable solid structure is formed, two or more of such sheets can be further combined and/or treated to form multi-layer porous dissolvable solid structure of any desirable three-dimensional shapes, including but not limited to: spherical, cubic, rectangular, oblong, cylindrical, rod, sheet, flower-shaped, fan-shaped, star-shaped, disc-shaped, and the like. The sheets can be combined and/or treated by any means known in the art, examples of which include but are not limited to, chemical means, mechanical means, and combinations thereof. Such combination and/or treatment steps are hereby collectively referred to as a "conversion" process, i.e., which functions to convert two or more porous dissolvable solid structures into a multi-layer porous dissolvable solid structure with a desired three-dimensional shape.

Conventional dissolvable solid articles have relatively high length/width-to-thickness ratios, i.e., they are relatively thin, in order to ensure fast dissolution of such articles in water. Therefore, such dissolvable solid articles are typically provided in form of relatively large but thin sheet products, which may be difficult to handle (e.g., too floppy and easily sticking together and hard to separate upon use) and are not aesthetically pleasing to the consumers. However, there is little or no space for change or improvement of such product form, due to constraints imparted by the dissolution requirement.

However, multi-layer porous solid structures formed by stacking multiple layers of the porous dissolvable solid structures together can be more dissolvable than single-layer solid structures that have the same aspect ratio. This allows significant extension of such multi-layer solid structures along the thickness direction, to create three-dimensional product shapes that are easier to handle and more aesthetically pleasing to the consumers (e.g., products in form of thick pads or even cubes).

A multilayer porous dissolvable solid structure formed by stacking multiple layers of porous dissolvable solid structures can be characterized by a maximum dimension D and a minimum dimension z (which is perpendicular to the maximum dimension), while the ratio of D/z (hereinafter also referred to as the "Aspect Ratio") ranges from 1 to about 10, from about 1.4 to about 9, from about 1.5 to about 8, or from about 2 to about 7. Note that when the Aspect Ratio is 1, the dissolvable solid article has a spherical shape. When the Aspect Ratio is about 1.4, the dissolvable solid article has a cubical shape.

The multilayer porous dissolvable solid structure may have, for example, a minimal dimension z that is about 3 mm to about 20 cm, from about 4 mm to about 10 cm, or from about 5 mm to about 30 mm.

The above described multi-layer porous dissolvable solid structures may comprise, for example, from about 2 to about 60, from about 4 to about 50, from about 5 to about 40, or from about 6 to about 30, of single layer porous dissolvable structures.

The multilayer dissolvable solid structure may comprise porous dissolvable solid structures of different colors, which are visual from an external surface (e.g., one or more side surfaces) of such multi-layer porous dissolvable solid structure. Such visible sheets of different colors can be aesthetically pleasing to the consumers. Further, the different colors may provide visual cues indicative of different benefit agents contained in the individual sheets. For example, the multilayer porous dissolvable solid structure may comprise a first sheet that has a first color and contains a first benefit agent and a second sheet that has a second color and contains a second benefit, while the first color provides a visual cue indicative of the first benefit agent, and while the second color provides a visual cue indicative of the second benefit agent.

Further, one or more functional ingredients can be "sandwiched" between individual sheets of the multilayer porous dissolvable solid structure as described hereinabove, e.g., by spraying, sprinkling, dusting, coating, spreading, dipping, injecting, or even vapor deposition. In order to avoid interference of such functional ingredients with the cutting seal or edge seal near the peripherals of the individual sheets, the functional ingredients can be located within a central region between two adjacent sheets, which is defined as a region that is spaced apart from the peripherals of such adjacent sheets by a distance that is at least 10% of the maximum Dimension D.

Test Methods

A) Determination of Average Pore Diameter

An Hitachi TM3000 Tabletop Microscope (S/N: 123104-04) is used to acquire SEM micrographs of samples. Samples of a porous dissolvable solid structure are approximately 1 cm×1 cm in area and cut from larger sheets. Images are collected at a magnification of 50×, and the unit is operated at 15 kV. A minimum of 5 micrograph images are collected from randomly chosen locations across each sample, resulting in a total analyzed area of approximately 43.0 mm$^2$ across which the average pore diameter is estimated.

The SEM micrographs are then firstly processed using the image analysis toolbox in Matlab. Where required, the images are converted to grayscale. For a given image, a histogram of the intensity values of every single pixel is generated using the 'imhist' Matlab function. Typically, from such a histogram, two separate distributions are obvious, corresponding to pixels of the brighter sheet surface and pixels of the darker regions within the pores. A threshold value is chosen, corresponding to an intensity value between the peak values of these two distributions. All pixels having an intensity value lower than this threshold value are then set to an intensity value of 0, while pixels having an intensity value higher are set to 1, thus producing a binary black and white image. The binary image is then analyzed using ImageJ (https://imagej.nih.gov, version 1.52a), to examine both the pore area fraction and pore size distribution. The scale bar of each image is used to provide a pixel/mm scaling factor. For the analysis, the automatic thresholding and the analyze particles functions are used to isolate each pore. Output from the analyze function includes the area fraction for the overall image and the pore area and pore perimeter for each individual pore detected.

Average Pore Diameter is defined as $D_A50$: 50% of the total pore area is comprised of pores having equal or smaller hydraulic diameters than the $D_A50$ average diameter.

Hydraulic diameter='4*Pore area (m$^2$)/Pore perimeter (m)'.

It is an equivalent diameter calculated to account for the pores not all being circular.

B) Determination of Regional Average Pore Size and Average Cell Wall Thickness

Porosity is the ratio between void-space to the total space occupied by the porous dissolvable solid structure. Porosity can be calculated from μCT scans by segmenting the void space via thresholding and determining the ratio of void voxels to total voxels. Similarly, solid volume fraction (SVF) is the ratio between solid-space to the total space, and SVF can be calculated as the ratio of occupied voxels to total voxels. Both Porosity and SVF are average scalar-values that do not provide structural information, such as, pore size distribution in the height-direction of the porous dissolvable solid structure, or the average cell wall thickness of the porous dissolvable solid structure struts.

To characterize the 3D structure of a porous dissolvable solid structure, samples are imaged using a μCT X-ray scanning instrument capable of acquiring a dataset at high isotropic spatial resolution. One example of suitable instrumentation is the SCANCO system model 50 μCT scanner (Scanco Medical AG, Brüttisellen, Switzerland) operated with the following settings: energy level of 45 kVp at 133 μA; 3000 projections; 15 mm field of view; 750 ms integration time; an averaging of 5; and a voxel size of 3 μm per pixel. After scanning and subsequent data reconstruction is complete, the scanner system creates a 16 bit data set, referred to as an ISQ file, where grey levels reflect changes in x-ray attenuation, which in turn relates to material density. The ISQ file is then converted to 8 bit using a scaling factor.

Scanned samples are normally prepared by punching a core of approximately 14 mm in diameter. The punch is laid flat on a low-attenuating foam and then mounted in a 15 mm diameter plastic cylindrical tube for scanning Scans of the samples are acquired such that the entire volume of all the mounted cut sample is included in the dataset. From this larger dataset, a smaller subvolume of the sample dataset is extracted from the total cross section of the scanned sample, creating a 3D slab of data, where pores can be qualitatively assessed without edge/boundary effects.

To characterize pore-size distribution in the height-direction, and the strut-size, Local Thickness Map algorithm, or LTM, is implemented on the subvolume dataset. The LTM Method starts with a Euclidean Distance Mapping (EDM) which assigns grey level values equal to the distance each void voxel is from its nearest boundary. Based on the EDM data, the 3D void space representing pores (or the 3D solid space representing struts) is tessellated with spheres sized to match the EDM values. Voxels enclosed by the spheres are assigned the radius value of the largest sphere. In other words, each void voxel (or solid voxel for struts) is assigned the radial value of the largest sphere that that both fits within the void space boundary (or solid space boundary for struts) and includes the assigned voxel.

The 3D labelled sphere distribution output from the LTM data scan can be treated as a stack of two dimensional images in the height-direction (or Z-direction) and used to estimate the change in sphere diameter from slice to slice as a function of sample depth. The strut thickness is treated as a 3D dataset and an average value can be assessed for the whole or parts of the subvolume. The calculations and measurements can be done using AVIZO Lite (9.2.0) from Thermo Fisher Scientific and MATLAB (R2017a) from Mathworks.

C) Percent Open Cell Content

The Percent Open Cell Content is measured via gas pycnometry. Gas pycnometry is a common analytical technique that uses a gas displacement method to measure volume accurately. Inert gases, such as helium or nitrogen, are used as the displacement medium. A sample of the porous dissolvable solid structure is sealed in the instrument compartment of known volume, the appropriate inert gas is admitted, and then expanded into another precision internal volume. The pressures before and after expansion are measured and used to compute the volume of the sample.

ASTM Standard Test Method D2856 provides a procedure for determining the percentage of open cells using an older model of an air comparison pycnometer. This device is no longer manufactured. However, one can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials. For these experiments, the samples can be analyzed using an Accupyc 1340 using nitrogen gas with the ASTM formpyc software. Method C of the ASTM procedure is to be used to calculate to percent open cells.

This method simply compares the geometric volume as determined using calipers and standard volume calculations to the open cell volume as measured by the Accupyc, according to the following equation:

Open cell percentage=Open cell volume of sample/
Geometric volume of sample*100

It is recommended that these measurements be conducted by Micromeritics Analytical Services, Inc. (One Micromeritics Dr, Suite 200, Norcross, Ga. 30093). More information on this technique is available on the Micromeritics Analytical Services web sites (www.particletesting.com or www.micromeritics.com), or published in "Analytical Methods in Fine particle Technology" by Clyde Orr and Paul Webb.

D) Final Moisture Content

Final moisture content of a porous dissolvable solid structure can be obtained by using a Mettler Toledo HX204 Moisture Analyzer (S/N B706673091). A minimum of 1 g of the sample is placed on the measuring tray. The standard program is then executed, with additional program settings of 10 minutes analysis time and a temperature of 110° C.

E) Thickness

Thickness of a porous dissolvable solid structure can be obtained by using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1-inch diameter platen weighing about 32 grams, which measures thickness at an application pressure of about 0.09 psi (6.32 gm/cm$^2$).

The thickness of a porous dissolvable solid structure can be measured by raising the platen, placing a section of the sample on the stand beneath the platen, carefully lowering the platen to contact the sample, releasing the platen, and measuring the thickness of the sample in millimeters on the digital readout. The sample should be fully extended to all edges of the platen to make sure thickness is measured at the lowest possible surface pressure, except for the case of more rigid substrates which are not flat.

F) Basis Weight of the Sheet Article

Basis Weight of a porous dissolvable solid structure can be calculated as the weight of the sample per area thereof (grams/m$^2$). The area is calculated as the projected area onto a flat surface perpendicular to the outer edges of the sample. The samples are cut into squares of 10 cm×10 cm, so the area is known. Each of such squares is then weighed, and the resulting weight is then divided by the known area of 100 cm$^2$ to determine the corresponding basis weight.

For a porous dissolvable solid structure of an irregular shape, if it is a flat object, the area is thus computed based on the area enclosed within the outer perimeter of such object. For a spherical object, the area is thus computed based on the average diameter as 3.14×(diameter/2)$^2$. For a cylindrical object, the area is thus computed based on the average diameter and average length as diameter×length. For an irregularly shaped three-dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (shaded-in for contrast) including a scale and using image analysis techniques.

G) Density

Density of a porous dissolvable solid structure can be determined by the equation: Calculated Density=Basis Weight of porous solid/(Porous Solid Thickness×1,000). The Basis Weight and Thickness of a porous dissolvable solid structure can be determined in accordance with the methodologies described hereinabove.

H) Specific Surface Area

The Specific Surface Area of a porous dissolvable solid structure can be measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then analyzed using an ASAP 2420 with krypton gas adsorption. It is recommended that these measurements be conducted by Micromeritics Analytical Services, Inc. (One Micromeritics Dr, Suite 200, Norcross, Ga. 30093). More information on this technique is available on the Micromeritics Analytical Services web sites (www.particletesting.com or www.micromeritics.com), or published in a book, "Analytical Methods in Fine Particle Technology", by Clyde Orr and Paul Webb.

Examples

The following examples further exemplify what is described herein. The examples are given solely for the purpose of illustration and are not to be construed as limitations, as many variations thereof are possible without departing from the spirit and scope. All exemplified amounts are concentrations by weight of the total pre-mixture, i.e., wt/wt percentages, unless otherwise specified.

The following surfactant/polymer liquid pre-mixtures are prepared at the indicated weight percentages as described below. The liquid formulations differ in the levels of amounts and types of isethionate primary surfactants (sodium cocoyl isethionate and sodium lauroyl methyl isethionate) anionic co-surfactants (sodium cocoyl glutamate, disodium laureth sulfosuccinate), and amphoteric surfactants (cocamidopropyl betaine, lauramidopropyl betaine, sodium lauroamphoacetate):

| Component | Ex. 1 | Ex. 2 | Ex. 3 | Ex. 4 | Ex. 5 |
|---|---|---|---|---|---|
| Glycerin[1] | 2.8 | 2.8 | 2.8 | 2.8 | 2.8 |
| Polyvinyl alcohol[2] | 8.3 | 8.3 | 8.3 | 8.3 | 8.3 |
| Sodium Cocoyl Isethionate[3] | 12.5 | 7.5 | 2.5 | 7.5 | 7.5 |
| Sodium Lauroyl Methyl Isethionate[4] | | | 10.0 | 5.0 | |
| Sodium Lauroamphoacetate (26% activity)[5] | | | | | |
| Cocamidopropyl betaine (31% activity)[6] | | | | | |

-continued

| Component | | | | | |
|---|---|---|---|---|---|
| Lauramidopropyl betaine (34% activity)[7] | 5.0 | 10.0 | 2.5 | 2.5 | 5.0 |
| Sodium Cocoyl Glutamate (39% activity)[8] | 2.5 | 2.5 | 5.0 | 5.0 | 2.5 |
| Disodium laureth sulfosuccinate (31% activity)[9] | | | | | 5.0 |
| Citric Acid[10] | 0.50 | 0.50 | 0.50 | 0.50 | 0.50 |
| Distilled water | Q.S. | Q.S. | Q.S. | Q.S. | Q.S. |

| Component | Ex. 6 | Ex. 7 | Ex. 8 | Ex. 9 | Ex. 10 |
|---|---|---|---|---|---|
| Glycerin[1] | 2.84 | 2.84 | 2.84 | 3.4 | 3.4 |
| Polyvinyl alcohol[2] | 8.3 | 8.3 | 8.3 | 10.0 | 10.0 |
| Sodium Cocoyl Isethionate[3] | 7.5 | 7.5 | 7.5 | 7.0 | 6.0 |
| Sodium Lauroyl Methyl Isethionate[4] | | | 5.0 | | |
| Sodium Lauroamphoacetate (26% activity)[5] | | | | | 4.0 |
| Cocamidopropyl betaine (31% activity)[6] | | | | | 4.0 |
| Lauramidopropyl betaine (34% activity)[7] | 7.5 | 7.5 | 7.5 | 10.0 | 6.0 |
| Sodium Cocoyl Glutamate (39% activity)[8] | 5.0 | 2.5 | | 3.0 | |
| Disodium laureth sulfosuccinate (31% activity)[9] | | 2.5 | | | |
| Citric Acid[10] | 0.50 | 0.50 | 0.50 | 0.50 | 0.50 |
| Distilled water | Q.S. | Q.S. | Q.S. | Q.S. | Q.S. |

| Component | Ex. 11 | Ex. 12 |
|---|---|---|
| Glycerin[1] | 3.4 | 3.4 |
| Polyvinyl alcohol[2] | 10.0 | 10.0 |
| Sodium Cocoyl Isethionate[3] | | |
| Sodium Lauroyl Methyl Isethionate[4] | 6.0 | 3.0 |
| Sodium Lauroamphoacetate (26% activity)[5] | 4.0 | 4.0 |
| Cocamidopropyl betaine (31% activity)[6] | | |
| Lauramidopropyl betaine (34% activity)[7] | 10.0 | 10.0 |
| Sodium Cocoyl Glutamate (39% activity)[8] | | |
| Disodium laureth sulfosuccinate (31% activity)[9] | | 3.0 |
| Citric Acid[10] | 0.50 | 0.50 |
| Distilled water | Q.S. | Q.S. |

[1]Superol K, USP FCC EP Glycerin, CAS: 56-81-5, supplier: Procter & Gamble Chemicals
[2]BP-17 with a viscosity of 21-26 cps and a % hydrolysis of 86-89%, CAS: 9002-89-5, supplier: Liwei Chemical Company LTD, China.
[3]JORDAPON SCI, CAS: 61789-32-0, supplier: BASF.
[4]ISELUX, CAS: 928663-45-0, supplier: Innospec Active Chemicals
[5]MIRANOL ULTRA L-32, CAS: 68608-66-2, supplier: McIntyre Group Ltd, University Park, IL,
[6]AMPHOSOL HCA-B, supplier: Stepan Company, Northfield, IL.
[7]MACKAM DAB-ULS, CAS: 4292-10-8, supplier: McIntyre Group Ltd, University Park, IL.
[8]EVERSOFT UCS-50SG, CAS: 68187-30-4, supplier: Sino Lion, New Jersey.
[9]MACKANATE EL P, CAS: 68815-56-5, supplier: Solvay,
[10]Citric Acid Anhydrous Fine Granular 51N, supplier: S.A. Citrique Beige N.V. Pastorijstraat 249, B-3300 Tienen, Belgium The above liquid pre-mixture compositions can be prepared with the use of a conventional overhead stirrer (IKA® RW20DZM Stirrer available from IKA® Works, Inc., Wilmington, Del.) and a hot plate (Corning Incorporated Life Sciences, Lowell, Mass.). Into an appropriately sized and cleaned vessel, the distilled water and glycerin are added with stirring at 100-150 rpm until homogenous. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 75 to 80° C. after which surfactants are added. The mixture is then heated to 85° C. while continuing to stir and then allowed to cool to room temperature. Additional distilled water is added to compensate for water lost to evaporation (based on the original tare weight of the container).

The porous dissolvable solid structures represented in Examples 13, 14, 15, 16, 17, 18, 19, 20, 21, 22, 23 and 24 are prepared from the surfactant/polymer liquid processing solutions from Examples 1, 2, 3, 4, 5, 6, 7, 8, 9, 10, 11, and 12, respectively, as described below.

Note: for simplicity, the formulations are displayed assuming bone dry conditions (0% relative humidity). However, the porous solids are hydroscopic and absorb moisture depending on the % relative humidity in the air. For example, at 50% relative humidity the below porous solids will comprise approximately 7 to 10% moisture.

| Component | Ex. 13 | Ex. 14 | Ex. 15 | Ex. 16 | Ex. 17 |
|---|---|---|---|---|---|
| Glycerin[1] | 9% | 9% | 9% | 9% | 9% |
| Polyvinyl alcohol[2] | 26.3% | 26.3% | 26.3% | 26.3% | 26.3% |
| Sodium Cocoyl Isethionate[3] | 39.6% | 23.7% | 7.9% | 23.7% | 23.7% |
| Sodium Lauroyl Methyl Isethionate[4] | 0.0% | 0.0% | 31.6% | 15.8% | 0.0% |
| Sodium Lauroamphoacetate (26% activity)[5] | 0.0% | 0.0% | 0.0% | 0.0% | 0.0% |
| Cocamidopropyl betaine (31% activity)[6] | 0.0% | 0.0% | 0.0% | 0.0% | 0.0% |
| Lauramidopropyl betaine (34% activity)[7] | 15.8% | 31.6% | 7.9% | 7.9% | 15.8% |
| Sodium Cocoyl Glutamate (39% activity)[8] | 7.9% | 7.9% | 15.8% | 15.8% | 7.9% |
| Disodium laureth sulfosuccinate (31% activity)[9] | 0.0% | 0.0% | 0.0% | 0.0% | 15.8% |
| Citric Acid[10] | 1.6% | 1.6% | 1.6% | 1.6% | 1.6% |

| Component | Ex. 18 | Ex. 19 | Ex. 20 | Ex. 21 | Ex. 22 |
|---|---|---|---|---|---|
| Glycerin[1] | 9% | 9% | 9% | 10% | 10% |
| Polyvinyl alcohol[2] | 26.2% | 26.2% | 26.2% | 29.5% | 29.5% |
| Sodium Cocoyl Isethionate[3] | 23.7% | 23.7% | 23.7% | 20.6% | 17.7% |
| Sodium Lauroyl Methyl Isethionate[4] | 0.0% | 0.0% | 15.8% | 0.0% | 0.0% |
| Sodium Lauroamphoacetate (26% activity)[5] | 0.0% | 0.0% | 0.0% | 0.0% | 11.8% |

| | | | | | |
|---|---|---|---|---|---|
| Cocamidopropyl betaine (31% activity)[6] | 0.0% | 0.0% | 0.0% | 0.0% | 11.8% |
| Lauramidopropyl betaine (34% activity)[7] | 23.7% | 23.7% | 23.7% | 29.5% | 17.7% |
| Sodium Cocoyl Glutamate (39% activity)[8] | 15.8% | 7.9% | 0.0% | 8.8% | 0.0% |
| Disodium laureth sulfosuccinate (31% activity)[9] | 0.0% | 7.9% | 0.0% | 0.0% | 0.0% |
| Citric Acid[10] | 1.6% | 1.6% | 1.6% | 1.5% | 1.5% |

| Component | Ex. 23 | Ex. 24 |
|---|---|---|
| Glycerin[1] | 10% | 10% |
| Polyvinyl alcohol[2] | 29.5% | 29.5% |
| Sodium Cocoyl Isethionate[3] | 0.0% | 0.0% |
| Sodium Lauroyl Methyl Isethionate[4] | 17.7% | 8.8% |
| Sodium Lauroamphoacetate (26% activity)[5] | 11.8% | 11.8% |
| Cocamidopropyl betaine (31% activity)[6] | 0.0% | 0.0% |
| Lauramidopropyl betaine (34% activity)[7] | 29.5% | 29.5% |
| Sodium Cocoyl Glutamate (39% activity)[8] | 0.0% | 0.0% |
| Disodium laureth sulfosuccinate (31% activity)[9] | 0.0% | 8.8% |
| Citric Acid[10] | 1.5% | 1.5% |

The porous dissolvable solid structures are prepared from the pre-mixture liquid processing solutions as follows. 10 ml of the pre-mixture is transferred at room temperature into an 80 ml graduated plastic beaker. The mixture is aerated using an IKA ULTRA-TURRAX® T 25 High speed mixer (available for instance from Hobart Corporation, Troy, Ohio) at 6,500 RPM until the slurry expands with entrained air to the 40 ml mark on the graduated beaker at a density of 0.25 g/cm$^3$. The resulting aerated mixture is then spread with a spatula into rectangle 40 mm×175 mm aluminum molds with a depth of 1.0 mm with the excess wet foam being removed with the straight edge of a metal spatula that is held at a 45 degree angle and slowly dragged uniformly across the mold surface. The aluminum molds are then placed on a hot plate with a pre-heated surface temperature of 100° C. and then left to dry for up to 30 minutes until the surface is dry to the touch. The molds are allowed to cool to room temperature with the substantially dry porous solid removed from the molds with the aid of a thin spatula and tweezers.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A porous dissolvable solid structure, comprising:
   a. from about 22% to about 41%, by weight of the porous dissolvable solid structure, of an isethionate surfactant selected from the group consisting of sodium cocoyl isethionate, sodium lauroyl methyl isethionate, or a combination thereof;
   b. from about 7% to about 25%, by weight of the porous dissolvable solid structure, of a non-sulfate anionic surfactant comprising sodium cocoyl glutamate, disodium laureth sulfosuccinate, or a combination thereof;
   c. from about 5% to about 25%, by weight of the porous dissolvable solid structure, lauramidopropyl betaine;
   d. from about 18% to about 38%, by weight of the porous dissolvable solid structure, of polyvinyl alcohol;
   e. from about 4.5% to about 20%, by weight of the porous dissolvable solid structure, of glycerin;
   wherein said porous dissolvable solid structure has a density of from about 0.05 g/cm$^3$ to about 0.20 g/cm$_3$; and
   wherein said porous dissolvable solid structure has a strain at break of 20 mm or more.

2. The porous dissolvable solid structure according to claim 1, wherein the isethionate surfactant is from about 22% to about 30%, by weight of the porous dissolvable solid structure; and the non-sulfate anionic surfactant is from about 15% to about 25%, by weight of the porous dissolvable solid structure.

3. The porous dissolvable solid structure according to claim 1, wherein the isethionate surfactant is from about 31% to about 41%, by weight of the porous dissolvable solid structure; and the non-sulfate anionic surfactant is from about 7% to about 18%, by weight of the porous dissolvable solid structure.

4. The porous dissolvable solid structure according to claim 1, wherein the isethionate surfactant is from about 38% to about 41%, by weight of the porous dissolvable solid structure; the non-sulfate anionic surfactant is from about 7% to about 17%, by weight of the porous dissolvable solid structure; and the lauramidopropyl betaine is from about 7% to about 17%, by weight of the porous dissolvable solid structure.

5. The porous dissolvable solid structure according to claim 4, wherein the isethionate surfactant is sodium cocoyl isethionate and the non-sulfate anionic surfactant comprises sodium cocoyl glutamate.

6. The porous dissolvable solid structure according to claim 4, wherein the isethionate surfactant is sodium lauroyl methyl isethionate and sodium cocoyl isethionate and the non-sulfate anionic surfactant comprises sodium cocoyl glutamate.

7. The porous dissolvable solid structure according to claim 1, wherein the isethionate surfactant is from about 22% to about 25%, by weight of the porous dissolvable solid structure and the non-sulfate anionic surfactant is from about 14% to about 17%, by weight of the porous dissolvable solid structure.

8. The porous dissolvable solid structure according to claim 1, wherein the isethionate surfactant is from about 22% to about 25%, by weight of the porous dissolvable solid structure and the non-sulfate anionic surfactant is from about 22% to about 25%, by weight of the porous dissolvable solid.

9. The porous dissolvable solid structure according to claim 8, wherein the isethionate surfactant is sodium cocoyl isethionate and the non-sulfate anionic surfactant comprises sodium cocoyl glutamate and disodium laureth sulfosuccinate.

10. The porous dissolvable solid structure according to claim 7, wherein the isethionate surfactant is sodium cocoyl isethionate and the non-sulfate anionic surfactant comprises sodium cocoyl glutamate.

11. The porous dissolvable solid structure according to claim 1, wherein the porous dissolvable solid structure comprises multiple layers.

12. The porous dissolvable solid of structure according to claim 1, wherein the total surfactant amount is from about 40% to about 70%, by weight of the porous dissolvable solid structure.

13. The porous dissolvable solid structure according to claim 1, wherein the porous dissolvable solid structure is an open celled foam.

14. The porous dissolvable solid structure according to claim 1, further comprising additional non-sulfate anionic surfactants comprising sodium lauroyl sarcosinate, lauryl sarcosine, cocoyl sarcosine, sodium lauroyl glutamate, disodium lauryl sulfosuccinate, sodium cocoyl taurate, sodium lauroyl taurate, sodium lauroyl lactylate, sodium cocoyl lactylate, sodium lauroyl glycinate, sodium cocoyl glycinate, or a combination thereof.

15. The porous dissolvable solid structure according to claim 1, further comprising zwitterionic surfactants comprising cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauryl betaine, lauryl hydroxysultaine, lauryl sultaine, or a combination thereof.

16. The porous dissolvable solid structure according to claim 1, further comprising zwitterionic surfactants comprising cocamidopropyl betaine, sodium lauroamphoacetate, sodium cocoamphoacetate, or a combination thereof.

* * * * *